US011857684B2

(12) United States Patent
Mehta

(10) Patent No.: US 11,857,684 B2
(45) Date of Patent: Jan. 2, 2024

(54) ORAL BILAYER TABLETS COMPRISING ACETYLSALICYLIC ACID AND PSEUDOEPHEDRINE, METHODS OF PREPARING AND USING THEREOF

(71) Applicant: Bayer Healthcare LLC, Whippany, NJ (US)

(72) Inventor: Harsh Mehta, Randolph, NJ (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 17/524,522

(22) Filed: Nov. 11, 2021

(65) Prior Publication Data

US 2022/0151936 A1    May 19, 2022

Related U.S. Application Data

(60) Provisional application No. 63/113,298, filed on Nov. 13, 2020.

(51) Int. Cl.
| | | |
|---|---|---|
| *A61K 9/24* | (2006.01) |
| *A61J 3/10* | (2006.01) |
| *A61K 31/137* | (2006.01) |
| *A61K 31/616* | (2006.01) |
| *A61K 9/20* | (2006.01) |

(52) U.S. Cl.
CPC ............... *A61K 9/209* (2013.01); *A61J 3/10* (2013.01); *A61K 31/137* (2013.01); *A61K 31/616* (2013.01); *A61K 9/2009* (2013.01); *A61K 9/2018* (2013.01); *A61K 9/2054* (2013.01); *A61K 9/2059* (2013.01)

(58) Field of Classification Search
None
See application file for complete search history.

(56) References Cited

U.S. PATENT DOCUMENTS

| 2,293,359 | A | 8/1942 | Sverre | |
|---|---|---|---|---|
| 5,665,388 | A | 9/1997 | Phykitt | |
| 6,284,269 | B1 | 9/2001 | Struengmann et al. | |
| 7,022,341 | B2 * | 4/2006 | Abelaira | A61K 31/135 424/464 |
| 11,135,188 | B2 * | 10/2021 | First | A61K 9/143 |
| 2003/0180352 | A1 | 9/2003 | Patel et al. | |
| 2005/0147668 | A1 | 7/2005 | Itai et al. | |
| 2006/0105039 | A1 | 5/2006 | Lai et al. | |
| 2007/0141144 | A1 | 6/2007 | Roberts et al. | |
| 2007/0218128 | A1 | 9/2007 | Bertelsen | |
| 2009/0311327 | A1 | 12/2009 | Roberts et al. | |
| 2013/0122098 | A1 | 5/2013 | First et al. | |
| 2015/0093439 | A1 * | 4/2015 | Lee | A61K 9/282 424/480 |

FOREIGN PATENT DOCUMENTS

| EP | 0414688 | A1 | 3/1991 |
|---|---|---|---|
| GB | 191225486 | A | 4/1913 |
| RU | 2099058 | C1 | 12/1997 |
| RU | 2170582 | C1 | 7/2001 |
| WO | 8907439 | A1 | 8/1989 |
| WO | 2005105102 | A1 | 11/2005 |
| WO | 2010132095 | A1 | 11/2010 |
| WO | 2018058009 | A1 | 3/2018 |

OTHER PUBLICATIONS

Eccles et al. "Analgesic and Decongestant Efficacy of the Combination of Aspirin with Pseudoephedrine in Patients With Symptoms of Upper Respiratory Tract Infection", Clin Pharmacol Drug Dev. Mar; 3(2):118-125, doi:10.1002/cpdd.39. Epub Aug. 20, 2013 (Year: 2013).*
Ansel, H. C. et al. (1999). "New Drug Development and Approval Process," Chapter 2 in Pharmaceutical Dosage Forms and Drug Delivery Systems, 7th edition, Balado, D. ed., Lippincott Williams and Wilkins, 3 pages.
Bosch, H. W. et al. (2008) "Pharmaceutical Applications of Finely Dispersed Systems," Medicinal Applications of Colloids pp. 69-93.
Date, A. A. et al. (2004, e-pub Oct. 21, 2004). "Current Strategies for Engineering Drug Nanoparticles," Current Opinion in Colloid & Interface Science 9:222-235.
Ely, L. et al. (2007, e-pub Nov. 7, 2006). "Effervescent Dry Powders for Respiratory Drug Delivery," European Journal of Pharmaceutics and Biopharmaceutics 65:346-353.
Extended European Search Report, dated Sep. 25, 2012, for Application No. EP10775187.7, filed May 11, 2009, 6 pages.
Horn, D. et al. (2001). "Organic Nanoparticles in the Aqueous Phase—Theory, Experiment, and Use," Angew. Chem. Int. Ed., 40:4330-4361.
Horter, D. et al. (2001). "Influence of Physicochemical Properties on Dissolution of Drugs in the Gastrointestinal Tract," Advanced Drug Delivery Reviews 46:75-87.
International Search Report and Written Opinion, dated Jul. 1, 2010, for Application No. PCT/US2010/001375, filed on May 10, 2010, 6 pages.
Javaid, K. A. et al. (Sep. 1972). "Dissolution of Aspirin from Tablets Containing Various Buffering Agents," Journal of Pharmaceutical Sciences 61(9):1370-1373.
Merisko-Liversidge, E. M. et al. (Jan. 2008). "Drug Nanoparticles: Formulating Poorly Water-Soluble Compounds," Toxicologic Pathology 36:43-48.

(Continued)

*Primary Examiner* — Susan T Tran
(74) *Attorney, Agent, or Firm* — MORRISON & FOERSTER LLP

(57) ABSTRACT

The present disclosure relates generally to bilayer tablets comprising a combination of two active pharmaceutical ingredients, and more specifically to bilayer tablets comprising acetylsalicylic acid, pseudoephedrine, and a dissolution aid. The bilayer tablets utilize a combination of granulated and non-granulated acetylsalicylic acid along with a unique distribution of sodium carbonate as a dissolution aid that provide acetylsalicylic acid and pseudoephedrine in a single dosage form having rapid dissolution and long-term storage stability (low degradation). The present disclosure also provides methods of preparing and of using the bilayer tablets.

20 Claims, 5 Drawing Sheets

(56) References Cited

OTHER PUBLICATIONS

Nikolic, L. et al. (Apr. 1992). "Influence of In Vitro Test Conditions on Release of Aspirin from Commercial Tablets," Journal of Pharmaceutical Sciences 81(4):386-391.

Orton, D. et al. (1979). "Plasma Salicylate Levels After Soluble and Effervescent Aspirin," British journal of Clinical Pharmacology 7(4):410-412.

Remington. (1990). "Pharmaceutical Sciences" 18th Edition, Mack Publishing Company, Easton, PA pp. 592-593, 3 pages.

Alderborn, G. (2001). "Dosage Form Design and Manufacture," Chapter 27 in Pharmaceutics: The Science of Dosage Form Design, Aulton, M. E. ed., Churchill Livingstone, pp. 397-417.

Anonymous. "Pseudoephedrine," located at <https://en.wikipedia.org/wiki/Pseudoephedrine#>, last visited on Jun. 7, 2023, 20 pages.

International Search Report and Written Opinion, dated Mar. 3, 2022, for Application No. PCT/US2021/057702, filed on Nov. 2, 2021, 18 pages.

Pimplaskar, H. K. (1994). "Study of Microencapsulated Products with Respect to their Ability to Prevent Incompatibilities," Open Access Master's Theses, University of Rhode Island, 106 pages.

\* cited by examiner

ORAL BILAYER TABLETS COMPRISING ACETYLSALICYLIC ACID AND PSEUDOEPHEDRINE, METHODS OF PREPARING AND USING THEREOF

CROSS-REFERENCE TO RELATED APPLICATION

This application claims priority to and the benefit of U.S. Provisional Application No. 63/113,298, filed on Nov. 13, 2020, the disclosure of which is incorporated herein by reference in its entirety.

FIELD

The present disclosure relates generally to bilayer tablets comprising a combination of two active pharmaceutical ingredients, and more specifically to bilayer tablets comprising acetylsalicylic acid, pseudoephedrine and a dissolution aid. The present disclosure also provides methods of preparing and methods of using the bilayer tablets described herein.

BACKGROUND

Due to the many symptoms and signs associated with the common cold and/or flu, individual active pharmaceutical ingredients taken by themselves are often insufficient to provide relief from the full catalog of symptoms, which can include, for example, nasal congestion, cough, fever/chills, muscle and/or body aches/pain, and fatigue. The use of two or more active pharmaceutical ingredients in combination may be appropriate to treat and address each symptom on an individual basis. However, for persons experiencing multiple symptoms simultaneously, having to take multiple medications containing individual active pharmaceutical ingredients at various times throughout a single day not only can be tedious and inconvenient, but may further result potential risk of improper dosing or other unintentional misuse.

Fixed-dose combination medications may provide a means to address multiple cold and/or flu symptoms in a single, compact dosage form, such as tablet, capsule or pill. For example, treatment with a combination dosage form containing both a decongestant, such as pseudoephedrine, and a dual antipyretic/analgesic, such as acetylsalicylic acid, could provide suitable relief in instances in which nasal congestion and/or sinus inflammation coincide with pain and fever.

However, the preparation of combination formulations may involve several considerations beyond the simple mixing of the individual active pharmaceutical ingredients into a single dosage form. Formulation of fixed-dose combinations often presents a number of difficulties in terms of maintaining the desired physicochemical and bioavailability properties that each active ingredient component would possess individually while ensuring their respective chemical stabilities when being prepared, stored and ultimately administered together. To circumvent these difficulties, many manufacturers simplify their formulation design by relying upon active pharmaceutical ingredients that are chemically compatible and have similar bioavailability profiles.

However, there still remains a need for formulations of fixed-dose combinations that combine two or more active pharmaceutical ingredients that may be chemically incompatible (such as acetylsalicylic acid and pseudoephedrine) in a compact, convenient, and quick-acting dosage form without compromising the therapeutic efficacy and/or storage stability of the individual active ingredients.

BRIEF SUMMARY

The present disclosure addresses the need for fixed-dose combinations for the treatment of cold and/or flu symptoms, such as sinus congestion in combination with fever and/or pain by providing a bilayer tablet comprising acetylsalicylic acid and pseudoephedrine, with each active pharmaceutical ingredient contained separately within one of the two distinct layers. By virtue of a combination of granulated and non-granulated acetylsalicylic acid within the acetylsalicylic acid layer with a unique distribution of a dissolution aid throughout the two layers, the bilayer tablets of the present disclosure achieve good storage stability and dissolution profiles.

In one aspect, provided herein is a bilayer tablet, comprising an acetylsalicylic acid layer, comprising: granules, wherein the granules comprise intragranular acetylsalicylic acid, intragranular sodium carbonate, and one or more intragranular excipients; extragranular acetylsalicylic acid; and one or more extragranular excipients; and a pseudoephedrine layer, comprising: pseudoephedrine or a pharmaceutically acceptable salt thereof; sodium carbonate; and one or more excipients; wherein 10-50% w/w of the total acetylsalicylic acid present in the tablet is intragranular acetylsalicylic acid, and wherein the tablet has a weight ratio of the acetylsalicylic acid to sodium carbonate of between 1:1 and 5:1.

In some embodiments of the present aspect, the tablet has a weight ratio of acetylsalicylic acid to sodium carbonate between 2:1 and 4:1. In other embodiments, which may be combined with the preceding embodiments, 10-50% w/w of the total sodium carbonate present in the tablet is intragranular sodium carbonate. In still other embodiments, which may be combined with any of the preceding embodiments, 20-40% w/w of the total acetylsalicylic acid present is intragranular acetylsalicylic acid. In yet other embodiments, which may be combined with any of the preceding embodiments, 20-40% w/w of the total sodium carbonate present in the tablet is present in the acetylsalicylic acid layer.

In some embodiments, the weight percentage of intragranular acetylsalicylic acid out of the total acetylsalicylic acid present is equal to the weight percentage of the intragranular sodium carbonate out of the total sodium carbonate present in the tablet. In certain embodiments, the bilayer tablets comprises between 250 mg and 1000 mg acetylsalicylic acid. In certain other embodiments, which may be combined with any of the preceding embodiments, the bilayer tablet comprises between 15 mg and 60 mg pseudoephedrine or a pharmaceutically acceptable salt thereof. In certain embodiments, the pseudoephedrine or a pharmaceutically acceptable salt thereof is pseudoephedrine hydrochloride.

In some embodiments, the one or more intragranular excipients in the granules comprises colloidal silicon dioxide. In other embodiments, the one or more extragranular excipients in the acetylsalicylic acid layer comprises colloidal silicon dioxide, cornstarch, and cellulose. In still other embodiments, the one or more excipients in the pseudoephedrine layer comprises mannitol, microcrystalline cellulose, cornstarch, and colloidal silicon dioxide. In yet other embodiments, the bilayer tablet comprises a coating.

In some embodiments, the tablet comprises less than or equal to 4% w/w salicylic acid of the initial acetylsalicylic acid content after storage at 50° C. and 65% relative humidity for at least 10 days. In other embodiments, the tablet comprises less than or equal to 4% w/w salicylic acid of the initial acetylsalicylic acid content after storage at 40° C. and 75% relative humidity for at least 1 month. In yet other embodiments, the tablet comprises at least 95% acetylsalicylic acid of the initial acetylsalicylic acid content after storage at 40° C. and 75% relative humidity for at least 1 month. In still further embodiments, the tablet has a dissolution profile wherein at least 85% acetylsalicylic acid and at least 85% pseudoephedrine are dissolved at 10 minutes as determined by USP Dissolution Test (Apparatus 1) in 50 mM sodium acetate buffer at pH 4.5 at 37±0.5° C.

In another aspect, provided herein is a method for preparing a bilayer tablet as described herein, comprising compacting and milling acetylsalicylic acid, sodium carbonate, and colloidal silicon dioxide to provide granules; combining the granules with acetylsalicylic acid, cornstarch, powdered cellulose, and colloidal silicon dioxide to provide an acetylsalicylic acid blend; combining pseudoephedrine or a pharmaceutically acceptable salt thereof, cornstarch, mannitol, sodium carbonate, microcrystalline cellulose and colloidal silicon dioxide to provide a pseudoephedrine blend; and compressing the acetylsalicylic acid blend and pseudoephedrine blend to form the bilayer tablet.

In some embodiments of this aspect, the method comprises compacting the acetylsalicylic acid, sodium carbonate, and colloidal silicon dioxide by roller compaction. In other embodiments of the present aspect, the granules have a particle size distribution wherein between 5% w/w and 30% w/w of the granules out of the total granule weight have a particle size of less than 150 μm, and wherein between 50% w/w and 80% w/w of the granules out of the total granule weight have a particle size of greater than 400 μm. In still further embodiments, the method further comprises drying the acetylsalicylic acid blend prior to compressing. In certain embodiments, the method comprises drying the acetylsalicylic acid blend to a water activity of less than or equal to 0.2. In some embodiments, the pseudoephedrine or a pharmaceutically acceptable salt thereof is pseudoephedrine hydrochloride.

In some embodiments, the method comprises compressing the acetylsalicylic acid blend and pseudoephedrine blend at a compression force between 1 kN and 30 kN. In some embodiments, the method comprises compressing the acetylsalicylic acid blend and pseudoephedrine blend at a compression force between 5 kN and 30 kN. In certain embodiments, the method comprises compressing the acetylsalicylic acid blend and pseudoephedrine blend at a compression force between 10 kN and 20 kN. In other embodiments, the method comprises compressing the acetylsalicylic acid blend at a first compression force to provide an acetylsalicylic acid layer; and compressing the pseudoephedrine blend on top of the acetylsalicylic acid layer at a second compression force to form the bilayer tablet. In yet other embodiments, compressing the pseudoephedrine blend at a first compression force to provide a pseudoephedrine layer; and compressing the acetylsalicylic acid blend on top of the pseudoephedrine layer at a second compression force to form the bilayer tablet. In certain embodiments, the first compression force is between 1 kN and 30 kN and the second compression force is between 5 kN and 30 kN. In certain embodiments, the first compression force is between 5 kN and 30 kN and the second compression force is between 5 kN and 30 kN. In still other embodiments, the method further comprises coating the tablet.

In yet another aspect, provided herein is a method for treating nasal congestion and pain or fever a in a human in need thereof, comprising administering a bilayer tablet as described herein to the human.

In still another aspect, provided herein is a package comprising a bilayer tablet as described herein. In some embodiments, the package further comprises a desiccant.

DESCRIPTION OF THE FIGURES

The present application can be understood by reference to the following description taken in conjunction with the accompanying figures.

FIG. 4A and FIG. 4B respectively depict the dissolution profiles of acetylsalicylic acid (percentage of acetylsalicylic acid dissolved) and pseudoephedrine hydrochloride (percentage of pseudoephedrine hydrochloride dissolved) as a function of time.

DETAILED DESCRIPTION

Figure 1:
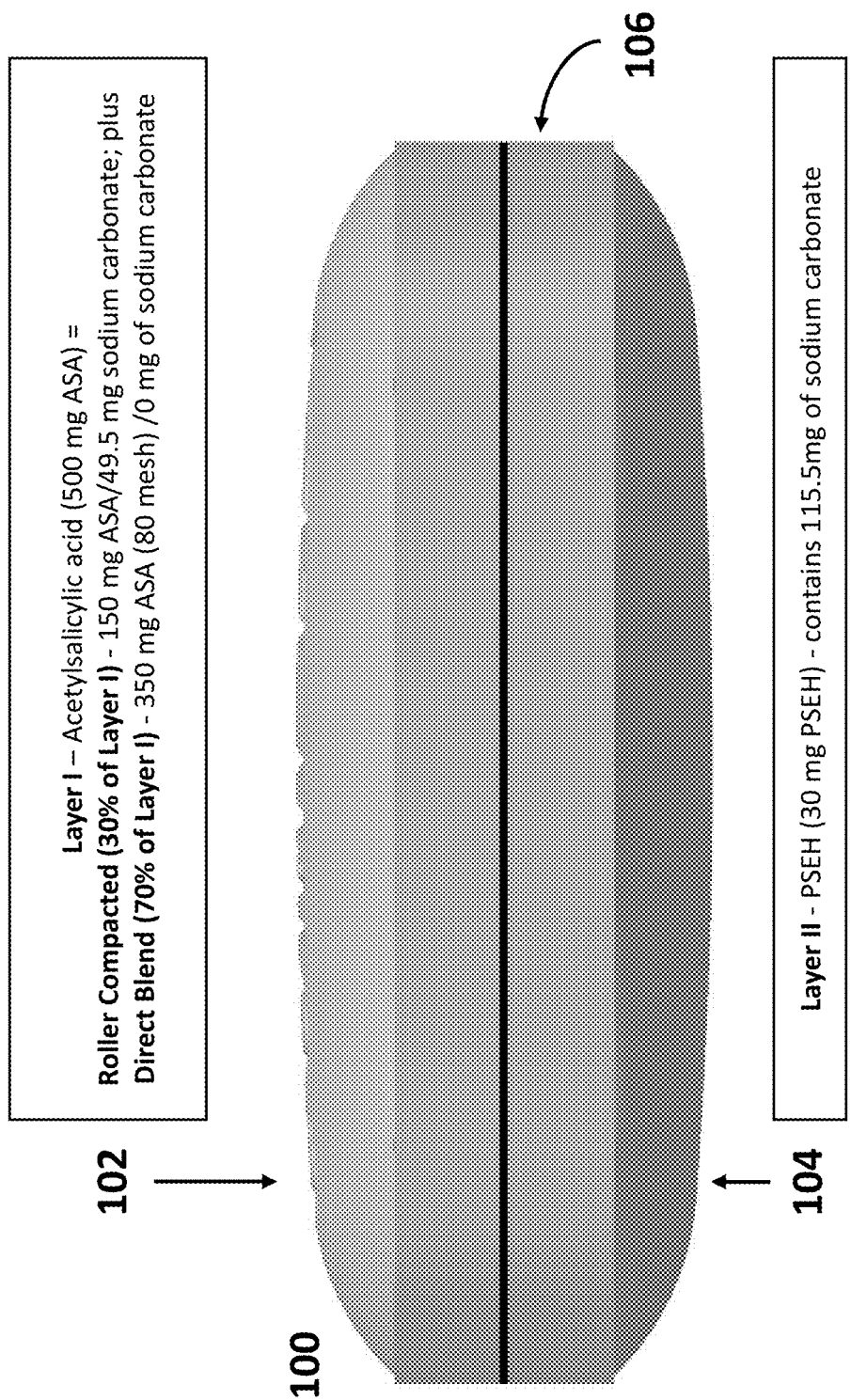
FIG. 1 depicts an exemplary schematic of a bilayer tablet comprising acetylsalicylic acid and pseudoephedrine.

Ailments like the common cold and flu often bring with them a multitude of symptoms, which are not all readily treated by a single active pharmaceutical ingredient. Fixed-dose combination formulations are one means of ameliorating multiple symptoms simultaneously to provide therapeutic relief with a single compact dosage form. However, the preparation of fixed-dose combinations is not a simple or straightforward process. Formulations containing a single active pharmaceutical ingredient are typically optimized with respect to a number of criteria, including but not limited to storage stability and drug dissolution and/or absorption rate, for the particular active pharmaceutical ingredient to be delivered. The combination of two or more active pharmaceutical ingredients requires careful thought as to how to accommodate the specific chemical instabilities of each component and mitigate any new formulation incompatibilities that may arise between the two or more active components.

For example, acetylsalicylic acid may be susceptible to hydrolysis degradation to form less stable free salicylic acid as well as other unwanted and/or inactive byproducts in the presence of water (such as residual moisture content introduced by excipients). Similarly, certain environmental and/or chemical conditions may degrade pseudoephedrine over time to produce less active or inactive derivatives. In addition to their individual susceptibilities to degradation, acetylsalicylic acid and pseudoephedrine may accelerate existing degradation pathways of the other active ingredients when combined, which may result in reduced therapeutic efficacy overall. Therefore, a major obstacle in preparing a fixed-dose combination is striking a balance of chemical and storage stability with the desired delivery properties while maintaining or improving the overall efficacy of both individual active ingredients in a single dosage form.

An additional concern with fixed-dose combinations, as with individual active pharmaceutical ingredients, is ensuring that the fixed-dose combinations demonstrate similar dissolution properties and rapid disintegration times in order to provide fast-acting relief from symptoms. While modifications may be made to address the storage stability and chemical compatibility of two or more active pharmaceutical ingredients, if the onset of action or symptomatic relief is not comparably as quick as would be provided with the individual dosage forms taken alone, consumers may be discouraged from using the fixed-dose combination.

For example, acetylsalicylic acid is also known to have limited solubility in water and under acidic conditions. The solubility of acetylsalicylic acid is increased under basic conditions, as in the gastrointestinal tract. The addition of basic dissolution aids to acetylsalicylic acid formulations may improve the solubility of acetylsalicylic acid within a given environment but can further expose acetylsalicylic acid to additional degradation and/or chemical rearrangement pathways to form less therapeutically active degradation products. For fixed-dose combinations, the concern is compounded by the difficulty in selecting suitable dissolution aids that are chemically compatible with each active ingredient and any excipients, achieving congruent dissolution times for the two or more active ingredients, and, thus also, a single dosage form having uniform dissolution and stability properties throughout.

Thus, there remains a need for fixed-dose combination dosage forms that achieve both storage stability and dissolution rate on par with the individual dosage forms of the relevant active pharmaceutical ingredients.

The present disclosure addresses this need by providing a fixed-dose combination dosage form that succeed in preserving the storage stability and dissolution rate for its component active pharmaceutical ingredients as observed in corresponding individual dosage forms. More specifically, provided herein is a bilayer tablet, comprising acetylsalicylic acid, pseudoephedrine or a pharmaceutically acceptable salt thereof, and a dissolution aid. The bilayer tablet possesses a unique internal architecture that ultimately provides a quick-acting, but storage stable formulation of acetylsalicylic acid and pseudoephedrine in a single dosage form.

The properties of the bilayer tablets described in the present disclosure are made possible by a combination of specific structural aspects utilized in the bilayer tablets. In order to achieve the desired stability and dissolution properties of both acetylsalicylic acid and pseudoephedrine in a single dosage form, the bilayer tablets employ two layers to separate the two actives from one another, a distribution of dissolution aids across the two layers, modification to the physical forms (e.g., granulated and non-granulated) of the acetylsalicylic acid present within the acetylsalicylic acid layer, and particular mass ratios of acetylsalicylic acid to the dissolution aid in the granules and the bilayer tablet as a whole.

As suggested by the term "bilayer", the bilayer tablet of the present disclosure utilizes two discrete layers, with one layer containing acetylsalicylic acid and the other containing pseudoephedrine. The separation of the two active pharmaceutical ingredients into two layers reduces the physical proximity and, thus, any chemical interaction between the two active components. With the incompatible active ingredients isolated from one another, the risk of accelerated degradation that may be caused by the combination of the two components is mitigated.

The bilayer tablet further employs a distribution of dissolution aid sodium carbonate across the two layers of the tablet and, within the acetylsalicylic acid layer, an admixture of granulated acetylsalicylic acid and non-granulated powder acetylsalicylic acid in the acetylsalicylic acid layer. As described above, dissolution aids such as sodium carbonate modulate the local environment of the dosage form and thus promote dissolution of the active pharmaceutical ingredient, e.g., acetylsalicylic acid. However, in the case of dissolution aids and acetylsalicylic acid, chemical reactions between the two components over time may also lead to the increased presence of degradation products. In the bilayer tablets provided herein, the dissolution aid is distributed across both layers of the tablet, e.g., with the majority of the dissolution aid in the pseudoephedrine layer. The allocation of the dissolution aid in this manner improves the dissolution profile of acetylsalicylic acid during administration (i.e., dissolves more rapidly) but reduces the extent of direct physical contact of acetylsalicylic acid with the dissolution aid in the acetylsalicylic acid layer itself and decreases the potential for undesired chemical interactions to occur.

Within the acetylsalicylic acid layer, the bilayer tablet utilizes a combination of acetylsalicylic acid in a non-granulated powder form with acetylsalicylic acid granules, wherein the dissolution aid present in the acetylsalicylic acid layer is restricted to the acetylsalicylic acid granules. The percentage of intragranular acetylsalicylic acid (provided in the granules) out of the total acetylsalicylic acid present is maintained within specific ranges (e.g., 10-50% w/w) to aid dissolution. Additionally, the ratio of acetylsalicylic acid to the dissolution aid(s) are controlled within certain mass ratio ranges, e.g., between 1:1 and 7:1, in both the granules and the bilayer tablet taken as a whole. The control over the quantities of acetylsalicylic acid and dissolution aids in the tablets as described above optimizes the effect of the dissolution aid where it directly contacts the acetylsalicylic acid by achieving minimal loss of the acetylsalicylic acid to degradation associated with the dissolution aids during storage with maximal dissolution of acetylsalicylic acid once administered.

By virtue of the compartmentalization of the active ingredients and dissolution aid(s), the bilayer tablets described herein provide fast-acting therapeutic benefit in a single, storage stable fixed-dose combination dosage form.

The following description sets forth exemplary methods, parameters and the like. It should be recognized, however, that such description is not intended as a limitation on the scope of the present disclosure but is instead provided as a description of exemplary embodiments.

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Bilayer Tablet

Provided herein is a fixed combination dosage form comprising two active pharmaceutical ingredients in a bilayer tablet, wherein each layer comprises one of the two active pharmaceutical ingredients, and both layers comprise one or more dissolution aids.

As described herein, a primary aspect of the bilayer tablets provided herein is the separation of active pharmaceutical ingredients, which may be chemically incompatible (e.g., reactive), into discrete layers. Reduction of the physical contact between active pharmaceutical ingredients that could induce or accelerate degradation enhances the storage stability of the active ingredients and the shelf life of the bilayer tablet.

In one aspect, provided herein is a bilayer tablet, wherein the bilayer tablet comprises a first layer and a second layer, wherein the first layer comprises a first active pharmaceutical ingredient, and wherein the second layer comprises a second active pharmaceutical ingredient. In some embodiments, the bilayer tablet comprises a first layer and a second layer, wherein the first layer comprises acetylsalicylic acid, and the second layer comprises pseudoephedrine or a pharmaceutically acceptable salt thereof. With reference to FIG. 1, schematic 100 is an exemplary schematic of a bilayer tablet comprising a first layer (acetylsalicylic acid (ASA) layer) 102 and a second layer (pseudoephedrine hydrochloride (PSEH) layer) 104. The acetylsalicylic acid layer 102 comprises a combination of granulated acetylsalicylic acid (e.g. roller-compacted granules) and non-granulated acetylsalicylic acid external to the granules (e.g., in a direct blend). As shown in FIG. 1, sodium carbonate is used as a dissolution aid and is incorporated in both layers 102 and 104. The sodium carbonate in the acetylsalicylic acid layer 102 is contained entirely within the granules. With reference again to FIG. 1, in some embodiments, the bilayer tablet further comprises an external lubricant or coating 106. In certain embodiments, the coating comprises a combination of hypromellose, zinc stearate and carnauba wax. In still further embodiments, the coating comprises a flavorant.

It should be recognized that the bilayer tablets of the present disclosure may also be suitable to deliver combinations of active pharmaceutical ingredients, wherein one or both analgesic/antipyretic and nasal decongestant active pharmaceutical ingredients is substituted with a therapeutically equivalent active ingredient. Such combinations may include, for example, naproxen or ibuprofen as analgesics/antipyretics in place of acetylsalicylic acid, phenylephrine as a nasal decongestant in lieu of pseudoephedrine, or any combinations thereof.

It should be further recognized that the bilayer tablets of the present disclosure may further comprise one or more additional active pharmaceutical ingredients in addition to acetylsalicylic acid and pseudoephedrine or a pharmaceutically salt thereof, provided the additional active ingredient is compatible with one or both of the acetylsalicylic acid and pseudoephedrine, and may be incorporated into one or both of the layers in the bilayer tablet. The inclusion of additional active pharmaceutical ingredients may be appropriate for the treatment of or provision of relief from other symptoms associated with the common cold and/or flu, such as sneezing or coughing.

In still further embodiments, the bilayer tablets of the present disclosure may be suitable to deliver any two active pharmaceutical ingredients for a fixed-dose combination treatment, especially combinations of active pharmaceutical ingredients that may exhibit similar potential for degradation due to external variables (moisture content) and/or share similar incompatibilities as acetylsalicylic acid and pseudoephedrine.

First Layer, or Acetylsalicylic Acid Layer

In some embodiments, the bilayer tablet of the present disclosure comprises a first layer, wherein the first layer comprises a first active pharmaceutical ingredient. In certain embodiments, the bilayer tablet comprises a first layer comprising an analgesic. In still further embodiments, the analgesic is acetylsalicylic acid. Alternatively, in some embodiments wherein the bilayer tablet comprises acetylsalicylic acid in the first layer, the first layer may be described as an acetylsalicylic acid layer.

Acetylsalicylic acid is a pain-relieving (analgesic) and fever-reducing (antipyretic) agent. Acetylsalicylic acid may also be used as an anti-inflammatory agent. As a result of its myriad effects, acetylsalicylic acid is widely used to treat various ailments, including those associated with the common cold and/or flu. Depending on the desired therapeutic effect to be provided by the bilayer tablet—that is, the extent to which the cold and flu symptoms are alleviated and how long relief is provided, the quantities of the active pharmaceutical ingredients, such as acetylsalicylic acid, contained in the bilayer tablet may vary.

The quantity of the acetylsalicylic acid present in the bilayer tablet may be expressed in terms of absolute milligram amounts. It should be recognized that the absolute milligram amounts of the present disclosure are intended to indicate the quantity of the acetylsalicylic acid in an individual bilayer tablet. In some embodiments, the bilayer tablet comprises at least 50 mg, at least 75 mg, at least 100 mg, at least 150 mg, or at least 250 mg acetylsalicylic acid. In other embodiments, the bilayer tablet comprises less than or equal to 1000 mg, less than or equal to 500 mg, less than or equal to 325 mg, or less than or equal to 250 mg acetylsalicylic acid.

Alternatively, the quantity of the acetylsalicylic acid may also be expressed as a weight percentage of the total weight of the bilayer tablet. In some embodiments, the bilayer tablet comprises at least 25% w/w, at least 30% w/w, at least 40% w/w, or at least 50% w/w acetylsalicylic acid by total weight of the bilayer tablet. In other embodiments, the bilayer tablet comprises less than or equal to 80% w/w, less than or equal to 75% w/w, less than or equal to 70% w/w, or less than or equal to 60% w/w acetylsalicylic acid by total weight of the bilayer tablet.

In still further embodiments, the bilayer tablet comprises acetylsalicylic acid, wherein the entirety of acetylsalicylic acid present in the bilayer tablet is contained with the first (acetylsalicylic acid) layer. In certain embodiments wherein the entirety of acetylsalicylic acid present in the bilayer tablet is contained with the first (acetylsalicylic acid) layer, the amount of acetylsalicylic acid present may be characterized by a weight percentage of the weight of the acetylsalicylic acid layer. For example, in some embodiments, the acetylsalicylic acid layer comprises at least 50% w/w, at least 60% w/w, at least 70% w/w, or at least 75% w/w acetylsalicylic acid by weight of the acetylsalicylic acid layer. In other embodiments, the bilayer tablet comprises less than or equal to 95% w/w, less than or equal to 90% w/w, or less than or equal to 85% w/w acetylsalicylic acid by weight of the acetylsalicylic acid layer.

As described above, the bilayer tablet of the present disclosure employs a combination of granulated and non-granulated acetylsalicylic acid within one of the layers of the bilayer tablet in order to achieve its observed storage stability and dissolution properties. In some embodiments, the acetylsalicylic acid present in the bilayer tablet may be further characterized by total quantity of acetylsalicylic acid, which is the sum of acetylsalicylic acid in granulated and non-granulated forms. In other embodiments, the bilayer tablet comprises granules, wherein at least a portion of the total acetylsalicylic acid present is contained within the granules (i.e., intragranular) and the remaining portion of the total acetylsalicylic acid is contained within the first layer external to the granules (i.e., extragranular).

Granules (Acetylsalicylic Acid Composite)

As described above, the bilayer tablets of the present disclosure comprise granules, wherein the granules comprise acetylsalicylic acid, the inclusion of which granules may lead to a faster absorption profile and improvement in the pharmacokinetic profile. The granules, which may collectively be referred to as an acetylsalicylic acid composite, also include one or more dissolution aids. It was observed that the incorporation of the acetylsalicylic acid composite comprising acetylsalicylic acid in intimate contact with one or more dissolution aids provided improvement in dissolution rate of the acetylsalicylic acid layer, particularly with respect to matching the dissolution profile of the active ingredient pseudoephedrine (or phenylephrine) in the second layer of the tablet. Without being bound to a particular theory of the invention, the envelopment of the acetylsalicylic acid by the dissolution aid and the smaller particle sizes of the ingredients are believed to lead to observed, significant improvement in the dissolution profile for the active pharmaceutical ingredient.

Additional benefits of the envelopment of acetylsalicylic acid by the dissolution aid include the protection of the granulated acetylsalicylic acid from adventitious moisture and the secondary behavior of dissolution aid to act like a starch or binder, thereby removing the need for additional fillers, binders and or stabilizers in the granules.

The quantity of acetylsalicylic acid present in the granules may be described as a weight percentage of the weight of the granules. In some embodiments, the granules comprise at least 50% w/w, at least 60% w/w, or at least 70% w/w acetylsalicylic acid by weight of the granules. In other embodiments, the granules comprise less than or equal to 90% w/w, less than or equal to 80% w/w, or less than or equal to 75% w/w acetylsalicylic acid by weight of the granules. In certain embodiments, the acetylsalicylic acid present in the granules may be referred to as intragranular acetylsalicylic acid.

In still other embodiments, the quantity of intragranular acetylsalicylic acid present in the granules may be described as a weight percentage of the weight of the acetylsalicylic acid layer. In some embodiments, the acetylsalicylic acid layer comprises at least 10% w/w, at least 15% w/w, or at least 20% w/w intragranular acetylsalicylic acid by weight of the acetylsalicylic acid layer. In other embodiments, the granules comprise less than or equal to 50% w/w, less than or equal to 40% w/w, or less than or equal to 30% w/w intragranular acetylsalicylic acid by weight of the acetylsalicylic acid layer.

In some embodiments, the granules comprise one or more dissolution aids. Dissolution aids, which may also be referred to as solubilizing agents or solubility enhancers, may enhance the dissolution profile of active pharmaceutical ingredients in a formulation. Suitable dissolution aids may include but are not limited to surfactants (e.g., sodium lauryl sulfate), magnesium hydroxide, magnesium oxide, aluminum oxide, calcium carbonate, sodium carbonate, sodium bicarbonate, or any combinations thereof. As with intragranular acetylsalicylic acid above, the dissolution aid present in the granules may be referred to as intragranular dissolution aid and characterized by a weight percentage of the weight of the granules.

In some embodiments, the granules comprise at least 5% w/w, at least 10% w/w, at least 15% w/w, or at least 20% w/w dissolution aid by weight of the granules. In other embodiments, the granules comprise less than or equal to 50% w/w, less than or equal to 40% w/w, or less than or equal to 30% w/w dissolution aid by weight of the granules.

In still further embodiments, the amount of intragranular dissolution aid may be described as a weight percentage of the weight of the acetylsalicylic acid layer. In some embodiments, the acetylsalicylic acid layer comprises at least 1% w/w, at least 2% w/w, at least 5% w/w, or at least 7% w/w intragranular dissolution aid by weight of the acetylsalicylic acid layer. In other embodiments, the acetylsalicylic acid layer comprises less than or equal to 15% w/w, less than or equal to 12% w/w, or less than or equal to 10% w/w intragranular dissolution aid by weight of the acetylsalicylic acid layer.

In some embodiments, the granules comprise sodium carbonate. In some embodiments, the granules comprise at least 5% w/w, at least 10% w/w, at least 15% w/w, or at least 20% w/w sodium carbonate by weight of the granules. In other embodiments, the granules comprise less than or equal to 50% w/w, less than or equal to 40% w/w, or less than or equal to 30% w/w sodium carbonate by weight of the granules. In some embodiments, the acetylsalicylic acid layer comprises at least 1% w/w, at least 2% w/w, at least 5% w/w, or at least 7% w/w intragranular sodium carbonate by weight of the acetylsalicylic acid layer. In other embodiments, the acetylsalicylic acid layer comprises less than or equal to 15% w/w, less than or equal to 12% w/w, or less than or equal to 10% w/w intragranular sodium carbonate by weight of the acetylsalicylic acid layer.

In other embodiments, the granules comprises one or more intragranular excipients in addition to the dissolution aid described above. Such intragranular excipients may be included in order to facilitate manufacture of the granules themselves or to modulate certain physical properties of the granules produced. Additional intragranular excipients apart from the dissolution aid(s) described above may include, but are not limited to, flow aids, diluents, binders, and disintegrants.

In some embodiments, the granules comprise a flow aid. Flow aids, also known as glidants, may be employed to reduce friction between powder or granular material and increase flowability. Exemplary flow aids include but are not limited to silicon dioxide, colloidal silicon dioxide, talc, magnesium stearate, zinc stearate, and stearic acid.

In some embodiments, the granules comprise colloidal silicon dioxide. In some embodiments, the granules comprise at least 0.1% w/w, at least 0.2% w/w, or at least 0.3% w/w colloidal silicon dioxide by weight of the granules. In other embodiments, the granules comprise less than or equal to 4% w/w, less than or equal to 2% w/w, or less than or equal to 1% w/w colloidal silicon dioxide by weight of the granules. In other embodiments, the acetylsalicylic acid layer comprises at least 0.03% w/w, at least 0.06% w/w, or at least 0.1% w/w intragranular colloidal silicon dioxide by weight of the acetylsalicylic acid layer. In other embodiments, the acetylsalicylic acid layer comprises less than or equal to 0.5% w/w, less than or equal to 1% w/w, or less than or equal to 2% w/w intragranular colloidal silicon dioxide by weight of the acetylsalicylic acid layer.

Extragranular Acetylsalicylic Acid and Other Excipients

In some embodiments, the first (acetylsalicylic acid) layer comprises additional active pharmaceutical ingredient outside of the granules described herein. Active pharmaceutical ingredient outside of the granules but contained within the first layer may be referred to herein as extragranular active pharmaceutical ingredient.

As described above, the bilayer tablets of the present disclosure utilize an admixture of acetylsalicylic acid in granulated and non-granulated form. The use of acetylsalicylic acid in both granulated and non-granulated forms contributes to the observed storage stability as well as the fast dissolution profile of the acetylsalicylic acid in the bilayer tablets. For example, in some embodiments wherein acetylsalicylic acid is the active pharmaceutical ingredient in the first layer (acetylsalicylic acid layer), the first layer comprises extragranular acetylsalicylic acid.

In some embodiments, the first layer comprises extragranular acetylsalicylic acid. In some embodiments, the acetylsalicylic acid layer comprises at least 30% w/w, at least 40% w/w, or at least 50% w/w extragranular acetylsalicylic acid by weight of the acetylsalicylic acid layer. In other embodiments, the acetylsalicylic acid layer comprises less than or equal to 80% w/w, less than or equal to 75% w/w, less than or equal to 70% w/w, or less than or equal to 60% w/w extragranular acetylsalicylic acid by weight of the acetylsalicylic acid layer.

In some embodiments, the first layer further comprises additional active pharmaceutical excipients outside of the granules described herein. As with acetylsalicylic acid described above, excipients present outside of the granules but contained within the first layer may be referred to herein as extragranular excipients.

In some embodiments wherein the first layer is an acetylsalicylic acid layer, the acetylsalicylic acid layer comprises one or more extragranular excipients. Similar to the intragranular excipients described above, extragranular excipients may be included in order to facilitate manufacture of the acetylsalicylic acid layer (e.g., flowability, ejection from tablet press) or to modulate certain physical properties of the acetylsalicylic acid layer produced (e.g., dissolution rate). In some embodiments, the one or more extragranular excipients comprise one or more extragranular binders (e.g, cellulose), one or more extragranular disintegrants (e.g., cornstarch), one or more extragranular glidants/flow aids (e.g., colloidal silicon dioxide), or any combinations thereof.

In some embodiments, the acetylsalicylic acid layer comprises one or more extragranular binders. Binders may be incorporated in the acetylsalicylic acid layer to help adhere the extragranular acetylsalicylic acid, granules and other extragranular excipients together. Binder excipients may also contribute to the overall volume or mechanical properties of the resulting formulation, that is, the acetylsalicylic acid layer. In certain embodiments, the one or more extragranular binders comprises cellulose. In certain embodiments, the acetylsalicylic acid layer comprises at least 1% w/w, at least 2% w/w, or at least 5% w/w cellulose by weight of the acetylsalicylic acid layer. In other embodiments, the acetylsalicylic acid layer comprise less than or equal to 15% w/w, less than or equal to 12% w/w, less than or equal to 10% w/w, or less than or equal to 7% w/w cellulose by weight of the acetylsalicylic acid layer.

In some embodiments, the acetylsalicylic acid layer comprises one or more extragranular disintegrants. Disintegrants are typically included in pharmaceutical formulations to aid in the dissolution process. Upon contact with moisture, disintegrants promote breakage of a solid dosage form into smaller pieces for more rapid solubilization. In certain embodiments, the one or more extragranular disintegrants comprises cornstarch. In some embodiments, the acetylsalicylic acid layer comprises at least 1% w/w, at least 2% w/w, or at least 5% w/w cornstarch by weight of the acetylsalicylic acid layer. In other embodiments, the acetylsalicylic acid layer comprise less than or equal to 15% w/w, less than or equal to 12% w/w, less than or equal to 10% w/w, or less than or equal to 7% w/w cornstarch by weight of the acetylsalicylic acid layer.

In still further embodiments, the acetylsalicylic acid layer comprises one or more extragranular glidants. Glidants may be incorporated to improve the flowability of extragranular acetylsalicylic acid, granules, and other extragranular excipients for easier manufacture and tableting. In certain embodiments, the one or more extragranular glidants comprises colloidal silicon dioxide. In certain embodiments, the acetylsalicylic acid layer comprises at least 0.1% w/w, at least 0.2% w/w, or at least 0.3% w/w colloidal silicon dioxide by weight of the acetylsalicylic acid layer. In other embodiments, the acetylsalicylic acid layer comprise less than or equal to 5% w/w, less than or equal to 2% w/w, or less than or equal to 1% w/w colloidal silicon dioxide by weight of the acetylsalicylic acid layer.

Distribution of Acetylsalicylic Acid in First Layer

As described above, the bilayer tablets of the present invention may comprise a total quantity of acetylsalicylic acid distributed within the first (acetylsalicylic acid) layer in either granulated or non-granulated form. The distribution of acetylsalicylic acid between granulated and non-granulated forms may influence the dissolution profile as well as the storage stability of the resulting acetylsalicylic acid layer, and thus, also, the final bilayer tablet. As described herein, it was observed that certain ratios of extragranular acetylsalicylic acid to intragranular acetylsalicylic acid in combination with distribution of a dissolution aid across two layers of a bilayer tablet resulted in rapid dissolution rate without compromising storage stability.

The amounts of granulated and non-granulated acetylsalicylic acid in the acetylsalicylic acid layer may be described as a percentage of the total acetylsalicylic acid present, or as a weight ratio of acetylsalicylic acid contained in the granules (that is, intragranular acetylsalicylic acid) to acetylsalicylic acid external to the granules (extragranular acetylsalicylic acid), or, conversely, a weight ratio of extragranular acetylsalicylic acid to intragranular acetylsalicylic acid.

In some embodiments, the distribution of acetylsalicylic acid in the first layer of the tablet is such that at least 40% w/w, at least 50% w/w, at least 60% w/w, or at least 70% w/w of the total acetylsalicylic acid present in the bilayer tablet is extragranular acetylsalicylic acid. In other embodiments, less than or equal to 90% w/w, less than or equal to 80% w/w, less than or equal to 70% w/w, or less than or equal to 60% w/w of the total acetylsalicylic acid present in the bilayer tablet is extragranular acetylsalicylic acid.

As described another way, in some embodiments, at least 10% w/w, at least 20% w/w, at least 30% w/w or at least 40% w/w of the total acetylsalicylic acid present in the bilayer tablet is intragranular acetylsalicylic acid. In other embodiments, the granules comprise less than or equal to 60% w/w, less than or equal to 50% w/w, less than or equal to 40% w/w, or less than or equal to 30% w/w of the total acetylsalicylic acid present in the bilayer tablet is intragranular acetylsalicylic acid.

In further embodiments, the ratio of extragranular acetylsalicylic acid to intragranular acetylsalicylic acid is at least about 40:60, at least about 50:50, at least about 60:40, or at least about 70:30. In still other embodiments, the ratio of extragranular acetylsalicylic acid to intragranular acetylsalicylic acid is less than or equal to 60:40, less than or equal to 70:30, less than or equal to 80:20, or less than or equal to 90:10.

Second Layer, or Pseudoephedrine Layer

In some embodiments, the bilayer tablet comprises a second layer, wherein the second layer comprises a second active pharmaceutical agent. In some embodiments, the bilayer tablet comprises a second layer, wherein the second layer comprises a decongestant. In certain embodiments, the decongestant is pseudoephedrine or a pharmaceutically acceptable salt thereof. In still certain other embodiments, the second layer comprises pseudoephedrine hydrochloride, or pseudoephedrine HCl. Alternatively, in some embodiments wherein the bilayer tablet comprises pseudoephedrine in the second layer, the second layer may be described as a pseudoephedrine layer.

The quantity of the pseudoephedrine (or other decongestant) present in the bilayer tablet may be expressed in terms of absolute milligram amounts. It should be recognized that the absolute milligram amounts of the present disclosure are intended to indicate the quantity of the pseudoephedrine in an individual bilayer tablet. In some embodiments, the bilayer tablet comprises at least 5 mg, at least 10 mg, at least 15 mg, at least 20 mg, or at least 30 mg pseudoephedrine or a pharmaceutically acceptable salt thereof. In other embodiments, the bilayer tablet comprises less than or equal to 240 mg, less than or equal to 120 mg, less than or equal to 100 mg, less than or equal to 80 mg, or less than or equal to 60 mg pseudoephedrine or a pharmaceutically acceptable salt thereof.

Alternatively, the quantity of the pseudoephedrine or a pharmaceutically acceptable salt thereof may also be expressed as a weight percentage of the total weight of the bilayer tablet. In some embodiments, the bilayer tablet comprises at least 1% w/w, at least 2% w/w, or at least 3% w/w pseudoephedrine or a pharmaceutically acceptable salt thereof. In other embodiments, the bilayer tablet comprises less than or equal to 24% w/w, less than or equal to 12% w/w, less than or equal to 10% w/w, less than or equal to 8% w/w, or less than or equal to 6% w/w pseudoephedrine or a pharmaceutically acceptable salt thereof.

In still further embodiments, the bilayer tablet comprises pseudoephedrine or a pharmaceutically acceptable salt thereof, wherein the entirety of pseudoephedrine or a pharmaceutically acceptable salt thereof present in the bilayer tablet is contained with the second (pseudoephedrine) layer. In certain embodiments wherein the entirety of pseudoephedrine or a pharmaceutically acceptable salt thereof present in the bilayer tablet is contained with the second (pseudoephedrine) layer, the amount of pseudoephedrine or a pharmaceutically acceptable salt thereof present may be characterized by a weight percentage of the weight of the pseudoephedrine layer. For example, in some embodiments, the pseudoephedrine layer comprises at least 2% w/w, at least 5% w/w, or at least 7% w/w pseudoephedrine or a pharmaceutically acceptable salt thereof by weight of the pseudoephedrine layer. In other embodiments, the bilayer tablet comprises less than or equal to 15% w/w, less than or equal to 12% w/w, or less than or equal to 10% w/w pseudoephedrine or a pharmaceutically acceptable salt thereof by weight of the pseudoephedrine layer.

As described above, the bilayer tablets of the present disclosure may utilize alternative nasal decongestants in lieu of pseudoephedrine. For example, in some embodiments, the second layer comprises phenylephrine or a pharmaceutically acceptable salt thereof in place of pseudoephedrine in a therapeutically equivalent amount. In other embodiments, the decongestant is phenylephrine or a pharmaceutically acceptable salt thereof. In certain embodiments, the second layer comprises phenylephrine hydrochloride, or phenylephrine HCl.

In some embodiments, the bilayer tablet comprises at least 5 mg, at least 10 mg, at least 20 mg, or at least 30 mg phenylephrine or a pharmaceutically acceptable salt thereof. In other embodiments, the bilayer tablet comprises less than or equal to 240 mg, less than or equal to 120 mg, less than or equal to 100 mg, less than or equal to 80 mg, or less than or equal to 60 mg phenylephrine or a pharmaceutically acceptable salt thereof.

Alternatively, the quantity of the phenylephrine or a pharmaceutically acceptable salt thereof may also be expressed as a weight percentage of the total weight of the bilayer tablet. In some embodiments, the bilayer tablet comprises at least 1% w/w, at least 2% w/w, or at least 3% w/w phenylephrine or a pharmaceutically acceptable salt thereof. In other embodiments, the bilayer tablet comprises less than or equal to 12% w/w, less than or equal to 10% w/w, less than or equal to 8% w/w, or less than or equal to 6% w/w phenylephrine or a pharmaceutically acceptable salt thereof.

In certain embodiments wherein the second layer comprises phenylephrine or a pharmaceutically acceptable salt thereof, the amount of phenylephrine or a pharmaceutically acceptable salt thereof present may be characterized by a weight percentage of the weight of the phenylephrine (second) layer. For example, in some embodiments, the phenylephrine layer comprises at least 2% w/w, at least 5% w/w, or at least 7% w/w phenylephrine or a pharmaceutically acceptable salt thereof by weight of the phenylephrine layer. In other embodiments, the bilayer tablet comprises less than or equal to 15% w/w, less than or equal to 12% w/w, or less than or equal to 10% w/w phenylephrine or a pharmaceutically acceptable salt thereof by weight of the phenylephrine layer.

As described above, the bilayer tablets incorporate a dissolution aid in the second (or pseudoephedrine) layer to accelerate the dissolution rate of the active ingredient (such as acetylsalicylic acid) in the first layer. By separating a fraction of the dissolution aid from acetylsalicylic acid, possible degradation induced by the interaction of the dissolution aid with acetylsalicylic acid is reduced significantly.

In some embodiments, the pseudoephedrine layer comprises a dissolution aid. Suitable dissolution aids may include but are not limited to magnesium hydroxide, magnesium oxide, aluminum oxide, calcium carbonate, sodium carbonate, sodium bicarbonate, or any combinations thereof. In some embodiments, the pseudoephedrine layer comprises at least 10% w/w, at least 20% w/w, or at least 30% w/w dissolution aid by weight of the pseudoephedrine layer. In other embodiments, the pseudoephedrine layer comprises less than or equal to 60% w/w, less than or equal to 50% w/w, or less than or equal to 40% w/w dissolution aid by weight of the pseudoephedrine layer.

In some embodiments, the pseudoephedrine layer comprises sodium carbonate. In some embodiments, the pseudoephedrine layer comprise at least 10% w/w, at least 20% w/w, or at least 30% w/w sodium carbonate. In other embodiments, the pseudoephedrine layer comprises less than or equal to 60% w/w, less than or equal to 50% w/w, or less than or equal to 40% w/w sodium carbonate.

In still further embodiments, the pseudoephedrine layer comprises one or more excipients in addition to sodium carbonate. In some embodiments, the one or more excipients in the pseudoephedrine layer comprise one or more diluents/fillers, one or more binders, one or more disintegrants, one or more glidants/flow aids, or any combinations thereof.

In some embodiments, the pseudoephedrine layer comprises one or more diluents. Diluents, which may also be known as fillers or thinners, are inactive ingredients that can be incorporated into the pseudoephedrine layer to improve flow and cohesion of formulations during manufacture, add to the bulk weight and improve content uniformity of the final formulation. Suitable diluents may include, for example, mannitol, lactose, microcrystalline cellulose, calcium phosphate, and pregelatinized starch. In some embodiments, the pseudoephedrine layer comprises mannitol. In some embodiments, the pseudoephedrine layer comprises at least 10% w/w, at least 20% w/w, or at least 30% w/w by weight of the pseudoephedrine layer. In other embodiments, the pseudoephedrine layer comprises less than or equal to 60% w/w, less than or equal to 50% w/w, or less than or equal to 40% w/w mannitol by weight of the pseudoephedrine layer.

In some embodiments, the pseudoephedrine layer comprises one or more binders. Binders may be incorporated in the pseudoephedrine layer to help adhere the pseudoephedrine or pharmaceutically acceptable salt thereof and other excipients together within the layer. Binder excipients may also contribute to the overall volume or mechanical properties of the resulting formulation, that is, the pseudoephedrine layer. Suitable binders for use in the pseudoephedrine layer may include, for example, microcrystalline cellulose, cellulose and starch. In certain embodiments, the one or more binders comprises microcrystalline cellulose (MCC). In certain embodiments, the pseudoephedrine layer comprises at least 5% w/w, at least 7% w/w, at least 10% w/w, or at least 12% w/w microcrystalline cellulose by weight of the pseudoephedrine layer. In other embodiments, the pseudoephedrine layer comprise less than or equal to 20% w/w, less than or equal to 17% w/w, or less than or equal to 15% w/w microcrystalline cellulose by weight of the pseudoephedrine layer.

In some embodiments, the pseudoephedrine layer comprises one or more disintegrants. As described above, disintegrants, such as cornstarch, crospovidone, and croscarmellose sodium, are typically included in pharmaceutical formulations to aid in the dissolution process. In certain embodiments, the one or more disintegrants comprises cornstarch. In some embodiments, the pseudoephedrine layer comprises at least 5% w/w, at least 7% w/w, at least 10% w/w, or at least 12% w/w cornstarch by weight of the pseudoephedrine layer. In other embodiments, the pseudoephedrine layer comprise less than or equal to 20% w/w, less than or equal to 17% w/w, or less than or equal to 15% w/w cornstarch by weight of the pseudoephedrine layer.

In still further embodiments, the pseudoephedrine layer comprises one or more glidants, such as colloidal silicon dioxide, silicon dioxide, talc, magnesium stearate, zinc stearate, and stearic acid. In certain embodiments, the one or more glidants comprises colloidal silicon dioxide. In certain embodiments, the pseudoephedrine layer comprises at least 0.1% w/w, at least 0.2% w/w, or at least 0.3% w/w colloidal silicon dioxide by weight of the pseudoephedrine layer. In other embodiments, the pseudoephedrine layer comprise less than or equal to 5% w/w, less than or equal to 2% w/w, or less than or equal to 1% w/w colloidal silicon dioxide by weight of the pseudoephedrine layer.

Total Dissolution Aid and Distribution in the Bilayer Tablet

As described herein, the bilayer structure of the tablets provided herein enables use of the acetylsalicylic acid and pseudoephedrine or a pharmaceutically acceptable salt thereof in a single dosage form, which mitigates or minimizes any unfavorable chemical interactions between the two actives in the tablet itself. The bilayer tablets of the present disclosure further utilize the bilayer structure of the tablet to take advantage of the improved solubilization of acetylsalicylic acid in basic media by using sodium carbonate as a dissolution aid but mitigating degradation pathways of acetylsalicylic acid while in storage. More specifically, the storage stability and dissolution rate achieved in the bilayer tablets of the present disclosure arise from the combination of the bilayer architecture with a distribution of dissolution aids across the two layers.

The total amount of dissolution aid present in the bilayer tablet may be considered as the sum of the amounts of dissolution aid present in each layer (i.e., intragranular dissolution aid in the acetylsalicylic acid layer and dissolution aid in the pseudoephedrine layer). The total dissolution aid present in the tablet may be described in absolute milligram quantities or in relative weight percentages of the total bilayer tablet weight.

In some embodiments, the bilayer tablet comprises at least 15 mg, at least 20 mg, at least 30 mg, or at least 50 mg dissolution aid. In other embodiments, the bilayer tablet comprises less than or equal to 300 mg, less than or equal to 150 mg, less than or equal to 100 mg, or less than or equal to 75 mg dissolution aid. In certain embodiments wherein the dissolution aid is sodium carbonate, the bilayer tablet comprises at least 15 mg, at least 20 mg, at least 30 mg, or at least 50 mg sodium carbonate. In certain other embodiments, the bilayer tablet comprises less than or equal to 300 mg, less than or equal to 150 mg, less than or equal to 100 mg, or less than or equal to 75 mg sodium carbonate.

In other embodiments, the bilayer tablet comprises at least 5% w/w, at least 10% w/w, or at least 15% w/w dissolution aid by total weight of the bilayer tablet. In yet other embodiments, the bilayer tablet comprises less than or equal to 25% w/w, less than or equal to 22% w/w, less than or equal to 20% w/w, or less than or equal to 17% w/w dissolution aid by total weight of the bilayer tablet. In yet further embodiments, the bilayer tablet comprises at least 5% w/w, at least 10% w/w, or at least 15% w/w sodium carbonate by total weight of the bilayer tablet. In still yet other embodiments, the bilayer tablet comprises less than or equal to 25% w/w, less than or equal to 22% w/w, less than or equal to 20% w/w, or less than or equal to 17% w/w sodium carbonate by total weight of the bilayer tablet.

The total dissolution aid is distributed within the bilayer tablet such that a fraction of the total sodium carbonate is directly combined with acetylsalicylic acid in granulate form and the remaining fraction is supplied in the second layer containing pseudoephedrine or a pharmaceutically acceptable salt thereof.

In some embodiments, the bilayer tablet comprises a dissolution aid, wherein at least 10%, at least 20%, at least 30%, or at least 40% of the total dissolution aid present is intragranular dissolution aid. In other embodiments, less than or equal to 100%, less than or equal to 90%, less than or equal to 80%, less than or equal to 70%, less than or equal to 60%, or less than or equal to 50% of the total dissolution aid present in the bilayer tablet is intragranular dissolution aid. In some embodiments, at least 10%, at least 20%, at least 30%, or at least 40% of the total dissolution aid present is present in the acetylsalicylic acid layer. In other embodiments, less than or equal to 100%, less than or equal to 90%, less than or equal to 80%, less than or equal to 70%, less than or equal to 60%, or less than or equal to 50% of the total dissolution aid present in the bilayer tablet is present in the acetylsalicylic acid layer.

In certain embodiments wherein the dissolution aid is sodium carbonate, at least 10%, at least 20%, at least 30%, or at least 40% of the total sodium carbonate present is intragranular sodium carbonate. In other embodiments, the less than or equal to 100%, less than or equal to 90%, less than or equal to 80%, less than or equal to 70%, less than or equal to 60%, or less than or equal to 50% of the total sodium carbonate present in the bilayer tablet is intragranular sodium carbonate. In some embodiments, at least 10%, at least 20%, at least 30%, or at least 40% of the total sodium carbonate present is present in the acetylsalicylic acid layer. In other embodiments, less than or equal to 100%, less than or equal to 90%, less than or equal to 80%, less than or equal to 70%, less than or equal to 60%, or less than or equal to 50% of the total sodium carbonate present in the bilayer tablet is present in the acetylsalicylic acid layer.

In some embodiments, the distribution of dissolution aid in bilayer tablet is such that the acetylsalicylic acid layer comprises at least 10%, at least 20%, at least 30%, or at least 40% of the total dissolution aid present in the bilayer tablet. In other embodiments, the acetylsalicylic acid layer comprises less than or equal to 100%, less than or equal to 90%, less than or equal to 80%, or less than or equal to 70% of the total dissolution aid present in the bilayer tablet.

In certain embodiments wherein the dissolution aid is sodium carbonate, the acetylsalicylic acid layer comprises at least 10%, at least 20%, at least 30%, or at least 40% of the total sodium carbonate present in the bilayer tablet. In other embodiments, the acetylsalicylic acid layer comprises less than or equal to 100%, less than or equal to 90%, less than or equal to 80%, or less than or equal to 70% of the total sodium carbonate present in the bilayer tablet.

In other embodiments, the pseudoephedrine layer comprises at least 10%, at least 20%, or at least 30% w/w of the total dissolution aid present in the bilayer tablet. In some embodiments, the pseudoephedrine layer comprises less than or equal to 90%, less than or equal to 80%, less than or equal to 70%, or less than or equal to 60% w/w of the total dissolution aid present in the bilayer tablet.

In still other embodiments wherein the dissolution aid is sodium carbonate, the pseudoephedrine layer comprises at least 10%, at least 20%, or at least 30% w/w of the total sodium carbonate present in the bilayer tablet. In some embodiments, the pseudoephedrine layer comprises less than or equal to 90%, less than or equal to 80%, less than or equal to 70%, or less than or equal to 60% w/w of the total sodium carbonate present in the bilayer tablet.

Weight Ratio of Acetylsalicylic Acid to Dissolution Aid

As briefly described above and further detailed below, the amount of intragranular acetylsalicylic acid relative to the total amount of acetylsalicylic acid and intragranular dissolution aid (such as sodium carbonate) relative to the total amount of dissolution aid may be modulated to achieve the desired stability and dissolution properties. Although the two parameters may be adjusted independently, it was observed that certain ratios, e.g., between about 1:1 and 7:1, of the total amount of acetylsalicylic acid to the total amount of dissolution aid (in both layers) produced the desired balance of reduced chemical instability and improved dissolution rates.

In some embodiments, the weight ratio of the total acetylsalicylic acid to total dissolution aid present in the bilayer tablet is at least about 1:1, at least about 2:1, at least about 3:1, or at least about 4:1. In other embodiments, the weight ratio of the total acetylsalicylic acid to total dissolution aid present in the bilayer tablet is less than or equal to about 7:1, less than or equal to about 6:1, less than or equal to about 5:1, or less than or equal to about 4:1. In still further embodiments, the weight ratio of the total acetylsalicylic acid to total dissolution aid present in the bilayer tablet is between about 1:1 and 7:1, between about 1:1 and 6:1, between about 1:1 and 5:1, between about 1:1 and 4:1, between about 2:1 and 7:1, between about 2:1 and 6:1, between about 2:1 and 5:1, between about 2:1 and 4:1, between about 3:1 and 7:1, between about 3:1 and 6:1, between about 3:1 and 5:1, or between about 3:1 and 4:1.

In certain embodiments wherein the dissolution aid is sodium carbonate, the weight ratio of the total acetylsalicylic acid to total sodium carbonate present in the bilayer tablet is at least about 1:1, at least about 2:1, at least about 3:1, or at least about 4:1. In other embodiments, the weight ratio of the total acetylsalicylic acid to total sodium carbonate present in the bilayer tablet is less than or equal to about 7:1, less than or equal to about 6:1, less than or equal to about 5:1, or less than or equal to about 4:1. In still further embodiments, the weight ratio of the total acetylsalicylic acid to total sodium carbonate present in the bilayer tablet is between about 1:1 and 7:1, between about 1:1 and 6:1, between about 1:1 and 5:1, between about 1:1 and 4:1, between about 2:1 and 7:1, between about 2:1 and 6:1, between about 2:1 and 5:1, between about 2:1 and 4:1, between about 3:1 and 7:1, between about 3:1 and 6:1, between about 3:1 and 5:1, or between about 3:1 and 4:1.

As also described above, the dissolution aid present in the acetylsalicylic acid layer is provided intragranularly, i.e., within the granules. In still further embodiments, the bilayer tablet comprises granules comprising acetylsalicylic acid and a dissolution aid, wherein the weight ratio of acetylsalicylic acid present in the granules to the dissolution aid present in the granules is at least about 1:1, at least about 2:1, at least about 3:1 or at least about 4:1. In other embodiments, the weight ratio of the acetylsalicylic acid present in the granules to the dissolution aid present in the granules is less than or equal to about 7:1, less than or equal to about 6:1, less than or equal to about 5:1, or less than or equal to about 4:1. In still further embodiments, the weight ratio of the acetylsalicylic acid present in the granules to the dissolution aid present in the granules is between about 1:1 and 7:1, between about 1:1 and 6:1, between about 1:1 and 5:1, between about 1:1 and 4:1, between about 2:1 and 7:1, between about 2:1 and 6:1, between about 2:1 and 5:1, between about 2:1 and 4:1, between about 3:1 and 7:1, between about 3:1 and 6:1, between about 3:1 and 5:1, or between about 3:1 and 4:1.

In certain embodiments wherein the dissolution aid is sodium carbonate, the bilayer tablet comprises granules comprising acetylsalicylic acid and sodium carbonate, wherein the weight ratio of acetylsalicylic acid present in the granules to the sodium carbonate present in the granules is at least about 1:1, at least about 2:1, at least about 3:1, or at least about 4:1. In other embodiments, the weight ratio of the acetylsalicylic acid present in the granules to the sodium carbonate present in the granules is less than or equal to about 7:1, less than or equal to about 6:1, less than or equal to about 5:1, or less than or equal to about 4:1. In still further embodiments, the weight ratio of the acetylsalicylic acid present in the granules to the sodium carbonate present in the granules is between about 1:1 and 7:1, between about 1:1 and 6:1, between about 1:1 and 5:1, between about 1:1 and 4:1, between about 2:1 and 7:1, between about 2:1 and 6:1, between about 2:1 and 5:1, between about 2:1 and 4:1, between about 3:1 and 7:1, between about 3:1 and 6:1, between about 3:1 and 5:1, or between about 3:1 and 4:1.

It should be recognized that the weight ratio of acetylsalicylic acid to dissolution aid present in the granules may be the same or different from the weight ratio of acetylsalicylic acid to dissolution aid in the bilayer tablet. For example in some embodiments, the weight ratio of the total acetylsalicylic acid to total sodium carbonate present in the bilayer tablet is between about 1:1 and 7:1 and the weight ratio of acetylsalicylic acid present in the granules to the sodium carbonate present in the granules is between about 1:1 and 7:1. In certain embodiments, the weight ratio of the total acetylsalicylic acid to total sodium carbonate present in the bilayer tablet and the weight ratio of acetylsalicylic acid present in the granules to the sodium carbonate present in the granules are the same. In other embodiments, the weight ratio of the total acetylsalicylic acid to total sodium carbonate present in the bilayer tablet and the weight ratio of acetylsalicylic acid present in the granules to the sodium carbonate present in the granules are the different. As described an alternative manner, in some embodiments, the weight percentage of intragranular acetylsalicylic acid out of the total acetylsalicylic acid present is 10-50% and the weight percentage of the intragranular sodium carbonate out of the total sodium carbonate is 10-50%. In certain embodiments, the weight percentage of intragranular acetylsalicylic acid out of the total acetylsalicylic acid present is equal to the weight percentage of the intragranular sodium carbonate out of the total sodium carbonate.

Properties of the Bilayer Tablet

As described herein, the bilayer tablets of the present disclosure may provide similar release profile, compatibility of active ingredients for storage, and long-term storage stability against degradation.

Dissolution Profile

In some embodiments, the bilayer tablet of the present disclosure may be characterized as immediate release. In some embodiments, the acetylsalicylic acid layer is immediate release. In other embodiments, the pseudoephedrine layer is immediate release. In certain embodiments, the acetylsalicylic acid layer and the pseudoephedrine layer are both immediate release. The tablet dissolution profiles were determined in accordance with the USP dissolution test (Apparatus 1, basket, 500 mL of pH 4.5, 50 mM sodium acetate buffer, at 37±0.5° C., rotation speed 50 rpm) (USP34-NF29 Chapter <711> Dissolution, Stage 6 Harmonization Bulletin dated Dec. 1, 2011).

In some embodiments, the bilayer tablet has a dissolution profile wherein at least 60%, at least 65%, at least 70%, at least 75%, at least 80%, or at least 85% of the total acetylsalicylic acid present in the tablet is dissolved after 10 minutes as determined by the USP Dissolution Test Apparatus-1 in 50 mM sodium acetate buffer at pH 4.5 and 37±0.5° C.

In other embodiments, the bilayer tablet has a dissolution profile wherein at least 40%, at least 45%, at least 50%, at least 55%, or at least 60% of the total pseudoephedrine or a pharmaceutically acceptable salt thereof is dissolved after 10 minutes as determined by the USP Dissolution Test Apparatus-1 in 50 mM sodium acetate buffer at pH 4.5 and 37±0.5° C.

In some embodiments, the bilayer tablet has a dissolution profile wherein at least 60%, at least 65%, at least 70%, at least 75%, at least 80%, or at least 85% of the total acetylsalicylic acid is dissolved and at least 40%, at least 45%, at least 50%, at least 55%, or at least 60% of the total pseudoephedrine or a pharmaceutically acceptable salt thereof is dissolved after 10 minutes as determined by the USP Dissolution Test Apparatus-1 in 50 mM sodium acetate buffer at pH 4.5 and 37±0.5° C.

In still further embodiments wherein phenylephrine or a pharmaceutically acceptable salt is employed in lieu of pseudoephedrine or a pharmaceutically acceptable salt thereof, the bilayer tablet has a dissolution profile wherein at least 40%, at least 45%, at least 50%, at least 55%, or at least 60% of the total phenylephrine or a pharmaceutically acceptable salt is dissolved after 10 minutes as determined by the USP Dissolution Test Apparatus-1 in 50 mM sodium acetate buffer at pH 4.5 and 37±0.5° C.

Stability to Degradation

As described herein, the bilayer tablets of the present disclosure combine a mixture of granulated and non-granulated acetylsalicylic acid with a unique distribution of sodium carbonate in the bilayer tablets to achieve a balanced dissolution profile and storage stability. The bilayer tablets incorporate sodium carbonate or other dissolution aids into the pseudoephedrine layer in order to facilitate quick dissolution of acetylsalicylic acid in dissolution media while minimizing intimate contact of acetylsalicylic acid with the dissolution air to reduce the extent of chemical degradation that may occur during storage.

The stability of the bilayer tablets to degradation may be characterized variously by the amount of the initial active pharmaceutical ingredients that remain or the quantity of degradation by-products that are observed within the tablet as a function of various storage conditions (e.g., temperature, humidity, and/or time). Evaluation of the stability of the bilayer tablets described herein may be carried out by various methods, which may include subjecting the tablets to precise temperature and/or humidity conditions for a duration of time and subsequently determining the presence and quantity of active pharmaceutical ingredients as well as any potential degradation products that may have formed under the evaluation conditions.

For example, in some embodiments, the bilayer tablets may be subjected to a storage temperature of at least about 20° C., at least about 25° C., at least about 30° C., at least about 40° C. or at least about 50° C. In other embodiments, the bilayer tablets are subjected to a storage temperature of less than or equal to 80° C., less than or equal to 75° C., less than or equal to 70° C., or less than or equal to 60° C. In still other embodiments, the bilayer tablets are subjected to a storage temperature of about 20° C., about 25° C., about 30° C., about 40° C., about 50° C., about 60° C., about 70° C., about 75° C., or about 80° C.

In some embodiments, any of which may be combined with any of the foregoing embodiments, the bilayer tablets are subjected to a storage humidity of at least about 30% relative humidity, at least about 40% relative humidity, at least about 50% relative humidity, or at least about 60% relative humidity. In other embodiments, the bilayer tablets are subjected to a storage humidity of less than or equal to about 100% relative humidity, less than or equal to about 90% relative humidity, less than or equal to about 80% relative humidity, less than or equal to about 75% relative humidity, or less than or equal to about 70% relative humidity.

In still further embodiments, the bilayer tablets are subjected to a storage at a temperature of about 25° C. and humidity of about 60% relative humidity (RH). In certain embodiments, the bilayer tablets are subjected to a storage at a temperature of about 40° C. and humidity of about 75% relative humidity. In other embodiments, the bilayer tablets are the bilayer tablets are subjected to a storage at a temperature of about 50° C. and humidity of between about 50% and about 70% relative humidity. In certain embodiments, the bilayer tablets are subjected to a storage at a temperature of about 50° C. and humidity of between about 50% and about 60% relative humidity or between about 60% and about 70% relative humidity. In still other embodiments, the bilayer tablets are subjected to a storage at a temperature of about 50° C. and humidity of 60% or 65% relative humidity.

In yet other embodiments, the bilayer tablets may be subjected to certain storage temperatures and relative humidities for at least about 1 day, at least about 2 days, at least about 3 days, at least about 4 days, at least about 5 days, at least about 10 days, at least about 20 days, at least 1 month, at least 1.5 months, at least 2 months, at least 3 months, or at least 6 months.

In still other embodiments, the bilayer tablets are stored with a desiccant. In other embodiments, the bilayer tablets are stored without a desiccant.

The storage stability and/or degree of degradation of the bilayer tablets provided herein may be characterized by the content of the two active pharmaceutical ingredients remaining after storage as well as the presence and content of degradation products after storage. The contents of the acetylsalicylic acid, pseudoephedrine or a pharmaceutically acceptable salt thereof, and their respective degradation products may be characterized in absolute quantities (such as total milligrams present) or in relative quantities (such as by weight percentage of the total weight of the tablet or as a molar percentage converted from the original acetylsalicylic acid and/or pseudoephedrine contents).

The stability of the bilayer tablet may be characterized by the preservation of acetylsalicylic acid and/or pseudoephedrine content remaining in the bilayer tablet after exposure to the aforementioned storage conditions. In some embodiments, the stability of the bilayer tablet may be characterized by the content of acetylsalicylic acid preserved after storage. In some embodiments, the bilayer tablet comprises at least 75%, at least 80%, at least 85%, at least 90%, at least 95%, at least 97% or at least 99% acetylsalicylic acid of the initial acetylsalicylic acid content after storage. In other embodiments, the bilayer tablet comprises less than or equal to 100%, less than or equal to 99%, less than or equal to 97%, or less than or equal to 95% acetylsalicylic acid of the initial acetylsalicylic acid content after storage. In still further embodiments, the bilayer tablet comprises between 75 and 100%, between 75 and 99%, between 75 and 97%, between 75 and 95%, between 80 and 100%, between 80 and 99%, between 80 and 97%, between 80 and 95%, between 85 and 100%, between 85 and 99%, between 85 and 97%, between 85 and 95%, between 90 and 100%, between 90 and 99%, between 90 and 97%, between 90 and 95%, between 95 and 100%, between 95 and 99%, between 95 and 97%, between 97 and 100%, between 97 and 99%, or between 99 and 100% acetylsalicylic acid of the initial acetylsalicylic acid content after storage.

In other embodiments, the bilayer tablet may be characterized by the absolute quantity of acetylsalicylic acid remaining after storage. For example, in some embodiments wherein the bilayer tablet has an initial acetylsalicylic acid content of 500 mg, the bilayer tablet comprises at least 375 mg, at least 400 mg, at least 425 mg, at least 450 mg, at least 475 mg, at least 485 mg, or at least 495 mg acetylsalicylic acid after storage. In other embodiments wherein the bilayer tablet has an initial acetylsalicylic acid content of 500 mg, the bilayer tablet comprises less than or equal to 495 mg, less than or equal to 485 mg, less than or equal to 475 mg, or less than or equal to 450 mg acetylsalicylic acid after storage. In still further embodiments wherein the bilayer tablet has an initial acetylsalicylic acid content of 500 mg, the bilayer tablet comprises between 375 mg and 500 mg, between 375 mg and about 495 mg, between 375 mg and 485 mg, between 375 mg and 475 mg, between 375 mg and 450 mg, between 400 mg and 500 mg, between 400 mg and about 495 mg, between 400 mg and 485 mg, between 400 mg and 475 mg, between 400 mg and 450 mg, between 425 mg and 500 mg, between 425 mg and about 495 mg, between 425 mg and 485 mg, between 425 mg and 475 mg, between 425 mg and 450 mg, between 450 mg and 500 mg, between 450 mg and about 495 mg, between 450 mg and 485 mg, between 450 mg and 475 mg, between 475 mg and 500 mg, between 475 mg and about 495 mg, between 475 mg and 485 mg, between 485 mg and 500 mg, between 485 mg and about 495 mg, or between 495 mg and 500 mg acetylsalicylic acid after storage.

In other embodiments, the stability of the bilayer tablet may be characterized by the content of pseudoephedrine (or a pharmaceutically acceptable salt thereof) preserved after storage. In some embodiments, the bilayer tablet comprises at least 75%, at least 80%, at least 85%, at least 90%, at least 95%, at least 97% or at least 99% pseudoephedrine of the initial pseudoephedrine content after storage. In other embodiments, the bilayer tablet comprises less than or equal to 100%, less than or equal to 99%, less than or equal to 97%, or less than or equal to 95% pseudoephedrine of the initial pseudoephedrine content. In still further embodiments, the bilayer tablet comprises between 75 and 100%, between 75 and 99%, between 75 and 97%, between 75 and 95%, between 80 and 100%, between 80 and 99%, between 80 and 97%, between 80 and 95%, between 85 and 100%, between 85 and 99%, between 85 and 97%, between 85 and 95%, between 90 and 100%, between 90 and 99%, between 90 and 97%, between 90 and 95%, between 95 and 100%, between 95 and 99%, between 95 and 97%, between 97 and 100%, between 97 and 99%, or between 99 and 100% pseudoephedrine of the initial pseudoephedrine content after storage.

As with acetylsalicylic acid, the content of pseudoephedrine or a pharmaceutically acceptable salt thereof may be characterized in absolute quantities after storage. In some embodiments wherein the bilayer tablet comprises an initial pseudoephedrine content of 30 mg, the bilayer tablet comprises at least 22 mg, at least 24 mg, at least 26 mg, at least 28 mg, or at least 29 mg pseudoephedrine or a pharmaceutically acceptable salt thereof after storage. In other embodiments wherein the bilayer tablet comprises an initial pseudoephedrine content of 30 mg, the bilayer tablet comprises less than or equal to 30 mg, less than or equal to 29 mg, less than or equal to 28 mg, or less than or equal to 26 mg pseudoephedrine or a pharmaceutically acceptable salt thereof after storage. In still further embodiments wherein the bilayer tablet has an initial pseudoephedrine content of 30 mg, the bilayer tablet comprises between 22 mg and 30 mg, between 22 mg and 29 mg, between 22 mg and 28 mg, between 22 mg and 26 mg, between 22 mg and 24 mg, 24 mg and 30 mg, between 24 mg and 29 mg, between 24 mg and 28 mg, between 24 mg and 26 mg, 26 mg and 30 mg, between 26 mg and 29 mg, between 26 mg and 28 mg, 28 mg and 30 mg, between 28 mg and 29 mg, or between 29 mg and 30 mg pseudoephedrine or a pharmaceutically acceptable salt thereof after storage.

It should be recognized that, when alternative active pharmaceutical ingredients are employed in lieu of acetylsalicylic acid and/pseudoephedrine or the pharmaceutically acceptable salt thereof or further active pharmaceutical ingredients are used in combination with acetylsalicylic acid and pseudoephedrine or a pharmaceutically acceptable salt thereof, the alternative and/or additional active ingredients may be similarly characterized by the remaining content present after storage. For example, in some embodiments wherein the bilayer tablet comprises phenylephrine or a pharmaceutically acceptable salt in lieu of pseudoephedrine, the bilayer tablet comprises at least 75%, at least 80%, at least 85%, at least 90%, at least 95%, at least 97% or at least 99% phenylephrine of the initial phenylephrine content after storage. In other embodiments, the bilayer tablet comprises less than or equal to 100%, less than or equal to 99%, less than or equal to 97%, or less than or equal to 95% phenylephrine of the initial phenylephrine content. In still further embodiments, the bilayer tablet comprises between 75 and 100%, between 75 and 99%, between 75 and 97%, between 75 and 95%, between 80 and 100%, between 80 and 99%, between 80 and 97%, between 80 and 95%, between 85 and 100%, between 85 and 99%, between 85 and 97%, between 85 and 95%, between 90 and 100%, between 90 and 99%, between 90 and 97%, between 90 and 95%, between 95 and 100%, between 95 and 99%, between 95 and 97%, between 97 and 100%, between 97 and 99%, or between 99 and 100% phenylephrine of the initial phenylephrine content after storage.

In some embodiments wherein the bilayer tablet comprises an initial phenylephrine content of 30 mg, the bilayer tablet comprises at least 22 mg, at least 24 mg, at least 26 mg, at least 28 mg, or at least 29 mg phenylephrine or a pharmaceutically acceptable salt thereof after storage. In other embodiments wherein the bilayer tablet comprises an initial phenylephrine content of 30 mg, the bilayer tablet comprises less than or equal to 30 mg, less than or equal to 29 mg, less than or equal to 28 mg, or less than or equal to 26 mg phenylephrine or a pharmaceutically acceptable salt thereof after storage. In still further embodiments wherein the bilayer tablet has an initial phenylephrine content of 30 mg, the bilayer tablet comprises between 22 mg and 30 mg, between 22 mg and 29 mg, between 22 mg and 28 mg, between 22 mg and 26 mg, between 22 mg and 24 mg, 24 mg and 30 mg, between 24 mg and 29 mg, between 24 mg and 28 mg, between 24 mg and 26 mg, 26 mg and 30 mg, between 26 mg and 29 mg, between 26 mg and 28 mg, 28 mg and 30 mg, between 28 mg and 29 mg, or between 29 mg and 30 mg phenylephrine or a pharmaceutically acceptable salt thereof after storage.

In still further embodiments, the stability of the bilayer tablet may be characterized by the presence and quantity of degradation products of acetylsalicylic acid and/or pseudoephedrine (or phenylephrine if present) in the tablet after exposure to the storage conditions. As described above, acetylsalicylic acid and pseudoephedrine may undergo various degradation processes to produce less active or inactive chemical compounds. The degradation products of acetylsalicylic acid and pseudoephedrine may be characterized on an individual basis as discrete chemical byproducts (e.g., salicylic acid or acetylsalicylsalicylic acid), on a combined basis as the byproducts of a single active pharmaceutical ingredient (e.g., total degradation products of acetylsalicylic acid, which may include but are not limited to salicylic acid and acetylsalicylsalicylic acid), or on as full basis as the total degradation products of both active pharmaceutical ingredients (e.g., the full set of degradation products observed for both acetylsalicylic acid and pseudoephedrine or a pharmaceutically acceptable salt thereof). Methods known in the art may be utilized to identify and quantify the degradation products present in the bilayer tablet including, for example, high performance liquid chromatography (HPLC) and ultraviolet (UV) absorption spectrometry. The table below shows the chemical structures of acetylsalicylic acid and a selection of its degradation products.

| Name of Compound | Structure of Compound |
|---|---|
| Acetylsalicylic Acid (ASA) | |
| (Free) Salicylic acid (FSA) | |
| Acetylsalicylsalicylic acid (ASSA) | |

A common hydrolytic degradation product of acetylsalicylic acid is free salicylic acid (also referred to herein as FSA, or as salicylic acid). The quantity of salicylic acid formed after exposure to particular storage and/or degradation conditions may be characterized as a weight or molar percentage of acetylsalicylic acid converted to salicylic acid from the original or initial acetylsalicylic acid (molar) content prior to being subjected to the specified degradation conditions. For example, a bilayer tablet as-prepared may contain 500 mg acetylsalicylic acid (initial acetylsalicylic acid content, 100 mol %) and, following a period of storage, a fraction of the initial acetylsalicylic acid content may have been converted to one or more degradation products. Following storage at a specified time, temperature, and/or humidity, the bilayer tablet may be observed to contain 95 mol % acetylsalicylic acid (475 mg) and 5 mol % salicylic acid (19.2 mg) of the initial acetylsalicylic acid content. Alternatively, the same degradation products may be described in terms of their weight percentage by weight of the initial acetylsalicylic acid content. For example, the bilayer tablet may be observed to contain 95% w/w acetylsalicylic acid (475 mg) by weight of the initial acetylsalicylic acid content and 3.8% w/w salicylic acid (19.2 mg) by weight of the initial acetylsalicylic acid content.

In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % salicylic acid of the initial acetylsalicylic acid content after storage. In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % salicylic acid of the initial acetylsalicylic acid content after storage at 50° C. and 60% relative humidity for at least 20 days.

In some embodiments, the bilayer tablet comprises less than or equal to 10% w/w less than or equal to 8% w/w, less than or equal to 6% w/w, less than or equal to 4% w/w, less than or equal to 2% w/w, or less than or equal to 1% w/w salicylic acid of the initial acetylsalicylic acid content after storage. In some embodiments, the bilayer tablet comprises less than or equal to 10% w/w, less than or equal to 8% w/w, less than or equal to 6% w/w, less than or equal to 4% w/w, less than or equal to 2% w/w, or less than or equal to 1% w/w salicylic acid of the initial acetylsalicylic acid content after storage at 50° C. and 60% relative humidity for at least 20 days.

In still other embodiments, the stability of the bilayer tablet may be characterized by the absolute quantity of free salicylic acid (FSA) present after storage. In some embodiments, the bilayer tablet comprises less than or equal to 5 mg, less than or equal to 10 mg, less than or equal to 15 mg, less than or equal to 20 mg, or less than or equal to 25 mg salicylic acid after storage.

Another degradation product of acetylsalicylic acid that may be observed is acetylsalicylsalicylic acid (also referred to herein as ASSA). Acetylsalicylsalicylic acid may be similarly characterized In some embodiments, the bilayer tablet comprises less than or equal to 1 mol %, less than or equal to 2 mol %, less than or equal to 3 mol %, less than or equal to 4 mol %, or less than or equal to 5 mol % acetylsalicylsalicylic acid of the initial acetylsalicylic acid content after storage. In some embodiments, the bilayer tablet comprises less than or equal to 1 mol %, less than or equal to 2 mol %, less than or equal to 3 mol %, less than or equal to 4 mol %, or less than or equal to 5 mol % acetylsalicylsalicylic acid of the initial acetylsalicylic acid content after storage at 50° C. and 60% relative humidity for at least 20 days.

In yet other embodiments, the bilayer tablet comprises less than or equal to 1% w/w, less than or equal to 2% w/w, less than or equal to 3% w/w, less than or equal to 4% w/w, or less than or equal to 5% w/w acetylsalicylsalicylic acid of the initial acetylsalicylic acid content after storage. In some embodiments, the bilayer tablet comprises less than or equal to 1% w/w, less than or equal to 2% w/w, less than or equal to 3 mol %, less than or equal to 4% w/w, or less than or equal to 5% w/w acetylsalicylsalicylic acid of the initial acetylsalicylic acid content after storage at 50° C. and 60% relative humidity for at least 20 days.

In still further embodiments wherein the bilayer tablet has an initial acetylsalicylic acid content of 500 mg, the bilayer tablet comprises less than or equal to 5 mg, less than or equal to 10 mg, less than or equal to 15 mg, less than or equal to 20 mg, or less than or equal to 25 mg acetylsalicylsalicylic acid (ASSA).

Additional byproducts of acetylsalicylic acid may form including free salicylic acid and acetylsalicylsalicylic acid as described herein and may contribute to the total amount of acetylsalicylic acid degradation byproducts formed in the bilayer tablet after exposure to certain storage conditions. It should be recognized that the bilayer tablets may be characterized by the amount of total degradation products, which can include but are not limited to salicylic acid, acetylsalicylsalicylic acid and others.

In some embodiments, the bilayer tablet comprises less than or equal to 1 mol %, less than or equal to 2 mol %, less than or equal to 3 mol %, less than or equal to 4 mol %, less than or equal to 5 mol %, less than or equal to 6 mol %, less than or equal to 7 mol %, less than or equal to 8 mol %, less than or equal to 9 mol %, or less than or equal to 10 mol % total degradation byproducts of acetylsalicylic acid of the initial acetylsalicylic acid content after storage. In other embodiments, the bilayer tablet comprises less than or equal to 1 mol %, less than or equal to 2 mol %, less than or equal to 3 mol %, less than or equal to 4 mol %, less than or equal to 5 mol %, less than or equal to 6 mol %, less than or equal to 7 mol %, less than or equal to 8 mol %, less than or equal to 9 mol %, or less than or equal to 10 mol % total degradation byproducts of acetylsalicylic acid of the initial acetylsalicylic acid content after storage at 50° C. and 60% relative humidity for at least 20 days.

In some embodiments, the bilayer tablet comprises less than or equal to 1% w/w, less than or equal to 2% w/w, less than or equal to 3% w/w, less than or equal to 4% w/w, less than or equal to 5% w/w, less than or equal to 6% w/w, less than or equal to 7% w/w, less than or equal to 8% w/w, less than or equal to 9% w/w, or less than or equal to 10% w/w total degradation byproducts of acetylsalicylic acid of the initial acetylsalicylic acid content after storage. In other embodiments, the bilayer tablet comprises less than or equal to 1% w/w, less than or equal to 2% w/w, less than or equal to 3% w/w, less than or equal to 4% w/w, less than or equal to 5% w/w, less than or equal to 6% w/w, less than or equal to 7% w/w, less than or equal to 8% w/w, less than or equal to 9% w/w, or less than or equal to 10% w/w total degradation byproducts of acetylsalicylic acid of the initial acetylsalicylic acid content after storage at 50° C. and 60% relative humidity for at least 20 days.

The stability of the bilayer tablet to degradation may be further characterized by the presence and/or quantity of pseudoephedrine degradation byproducts. It should also be recognized that bilayer tablets comprising phenylephrine or a pharmaceutically acceptable salt thereof in lieu of pseudoephedrine may also be characterized as described below but for phenylephrine and its degradation products. Pseudoephedrine or pharmaceutically acceptable salts thereof may undergo degradation pathways to form, for example, N-acetyl pseudoephedrine (PSEH N-acetyl or PSEH N-ester), O-acetyl pseudoephedrine (PSEH O-acetyl or PSEH O-ester) and N,O-diacetyl pseudoephedrine (PSEH N,O-diacetyl or PSEH diester). The table below shows the chemical structure of pseudoephedrine hydrochloride and a selection of its degradation products.

| Name of Compound | Structure of Compound |
| --- | --- |
| Pseudoephedrine Hydrochloride (PSEH) | 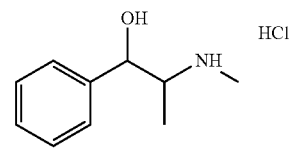 |
| O-Acetyl pseudoephedrine (PSEH O-acetyl) | 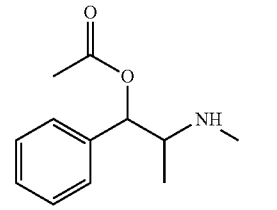 |
| N-Acetyl pseudoephedrine (PSEH N-acetyl) | 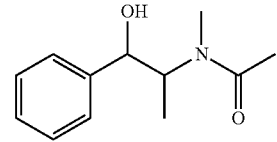 |

| Name of Compound | Structure of Compound |
|---|---|
| N,O-Diacetyl pseudoephedrine (PSEH N,O-diacetyl) | (chemical structure) |

In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % N-acetyl pseudoephedrine of the initial pseudoephedrine content after storage. In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % N-acetyl pseudoephedrine of the initial pseudoephedrine content after storage at 50° C. and 60% relative humidity for at least 10 days.

In some embodiments, the bilayer tablet comprises less than or equal to 10% w/w, less than or equal to 8% w/w, less than or equal to 6% w/w, less than or equal to 4% w/w, less than or equal to 2% w/w, or less than or equal to 1% w/w N-acetyl pseudoephedrine of the initial pseudoephedrine content after storage. In some embodiments, the bilayer tablet comprises less than or equal to 10% w/w, less than or equal to 8% w/w, less than or equal to 6% w/w, less than or equal to 4% w/w, less than or equal to 2% w/w, or less than or equal to 1% w/w N-acetyl pseudoephedrine of the initial pseudoephedrine content after storage at 50° C. and 60% relative humidity for at least 10 days.

In other embodiments wherein the bilayer tablet has an initial pseudoephedrine content of 30 mg, the bilayer tablet comprises less than or equal to 10 mg, less than or equal to 8 mg, less than or equal to 6 mg, less than or equal to 4 mg, or less than or equal to 2 mg N-acetyl pseudoephedrine after storage.

In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % O-acetyl pseudoephedrine of the initial pseudoephedrine content after storage. In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % O-acetyl pseudoephedrine of the initial pseudoephedrine content after storage at 50° C. and 60% relative humidity for at least 10 days.

In some embodiments, the bilayer tablet comprises less than or equal to 10% w/w, less than or equal to 8% w/w, less than or equal to 6% w/w, less than or equal to 4% w/w, less than or equal to 2% w/w, or less than or equal to 1% w/w O-acetyl pseudoephedrine of the initial pseudoephedrine content after storage. In some embodiments, the bilayer tablet comprises less than or equal to 10% w/w, less than or equal to 8% w/w, less than or equal to 6% w/w, less than or equal to 4% w/w, less than or equal to 2% w/w, or less than or equal to 1% w/w O-acetyl pseudoephedrine of the initial pseudoephedrine content after storage at 50° C. and 60% relative humidity for at least 10 days.

In other embodiments wherein the bilayer tablet has an initial pseudoephedrine content of 30 mg, the bilayer tablet comprises less than or equal to 10 mg, less than or equal to 8 mg, less than or equal to 6 mg, less than or equal to 4 mg, or less than or equal to 2 mg O-acetyl pseudoephedrine after storage.

In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % N,O-diacetyl pseudoephedrine of the initial pseudoephedrine content after storage. In some embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % N,O-diacetyl pseudoephedrine of the initial pseudoephedrine content after storage at 50° C. and 60% relative humidity for at least 10 days.

In some embodiments, the bilayer tablet comprises less than or equal to 10% w/w, less than or equal to 8% w/w, less than or equal to 6% w/w, less than or equal to 4 mol %, less than or equal to 2% w/w, or less than or equal to 1% w/w N,O-diacetyl pseudoephedrine of the initial pseudoephedrine content after storage. In some embodiments, the bilayer tablet comprises less than or equal to 10% w/w, less than or equal to 8% w/w, less than or equal to 6 mol %, less than or equal to 4% w/w, less than or equal to 2% w/w, or less than or equal to 1% w/w N,O-diacetyl pseudoephedrine of the initial pseudoephedrine content after storage at 50° C. and 60% relative humidity for at least 10 days.

In other embodiments wherein the bilayer tablet has an initial pseudoephedrine content of 30 mg, the bilayer tablet comprises less than or equal to 10 mg, less than or equal to 8 mg, less than or equal to 6 mg, less than or equal to 4 mg, or less than or equal to 2 mg N,O-diacetyl pseudoephedrine after storage.

The various degradation byproducts of pseudoephedrine or a pharmaceutically acceptable salt thereof may be considered in aggregate as the total degradation byproducts of pseudoephedrine. In still further embodiments, the bilayer tablet comprises less than or equal to 10 mol %, less than or equal to 8 mol %, less than or equal to 6 mol %, less than or equal to 4 mol %, less than or equal to 2 mol %, or less than or equal to 1 mol % total degradation byproducts of pseudoephedrine or a pharmaceutically acceptable salt thereof of the initial pseudoephedrine content after storage.

In other embodiments wherein the bilayer tablet has an initial pseudoephedrine content of 30 mg, the bilayer tablet comprises less than or equal to 10 mg, less than or equal to 8 mg, less than or equal to 6 mg, less than or equal to 4 mg, or less than or equal to 2 mg total degradation byproducts of pseudoephedrine or a pharmaceutically acceptable salt thereof after storage.

Methods of Preparing the Bilayer Tablet

In another aspect, provided herein are methods for preparing the bilayer tablets as described herein.

Figure 2:
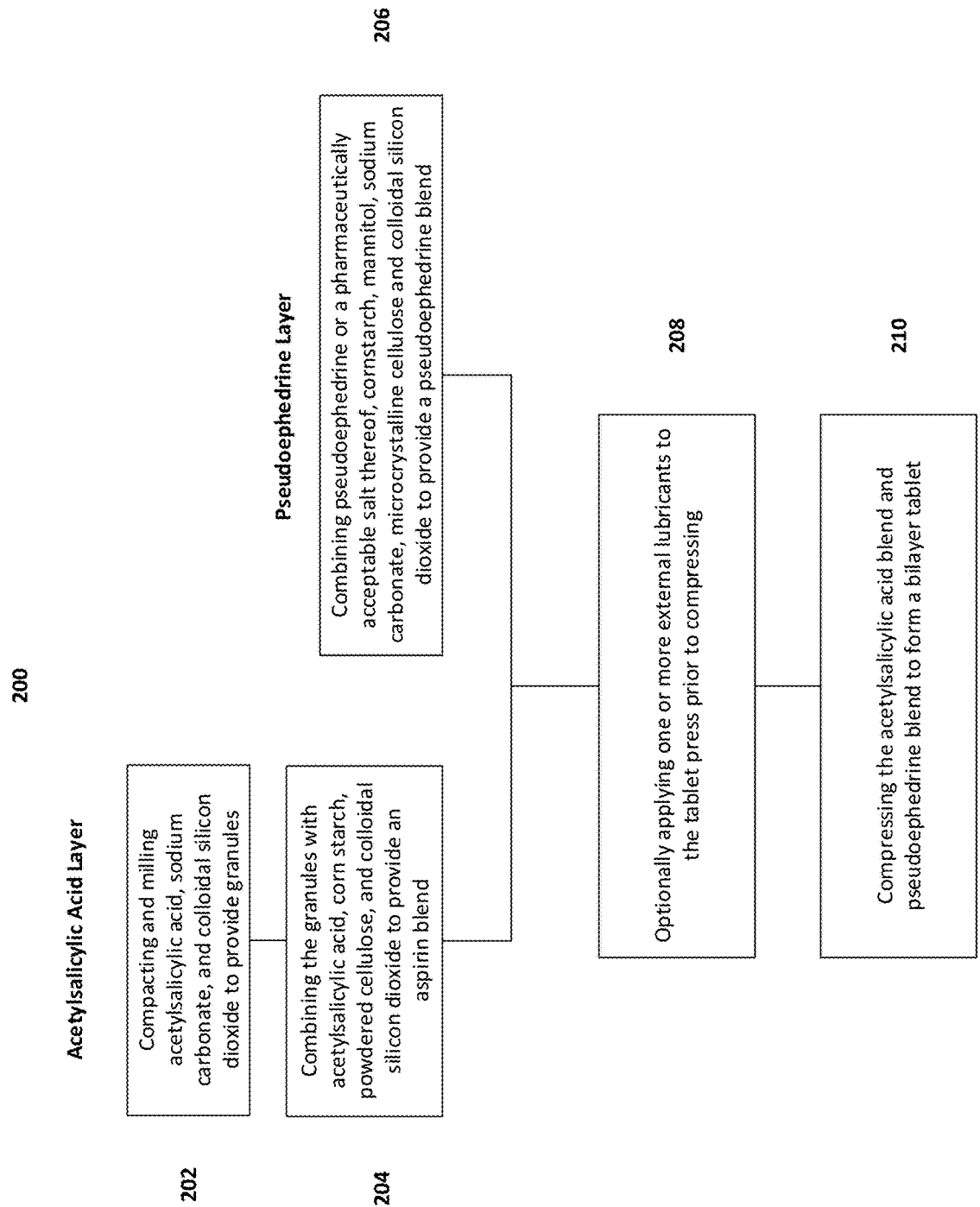
FIG. 2 depicts an exemplary process for preparing a bilayer tablet comprising acetylsalicylic acid and pseudoephedrine.

With reference to FIG. 2, process 200 is an exemplary process for preparing a bilayer tablet as described herein. In step 202, acetylsalicylic acid is compacted and milled with sodium carbonate and colloidal silicon dioxide to form granules. The resulting granules are further combined with (non-granulated) acetylsalicylic acid and extragranular excipients in step 204, thereby providing an acetylsalicylic acid blend. The acetylsalicylic acid blend corresponds to the acetylsalicylic acid layer in the final bilayer tablet. In parallel step 206, pseudoephedrine, sodium carbonate and additional excipients are combined to provide a pseudoephedrine blend. The pseudoephedrine blend corresponds to the pseudoephedrine layer in the bilayer tablet. Following preparation of the acetylsalicylic acid blend and the pseudoephedrine blend, the two blends are passed to a tablet press to be compressed. The tablet press may optionally be treated with external lubrication to facilitate the pressing of the tablet as provided in step 208. The acetylsalicylic acid blend and pseudoephedrine blend are subsequently compressed to form the bilayer tablet in step 210.

It should be recognized that the exemplary process 200 may be adapted to accommodate alternative active pharmaceutical ingredients, dissolution aids and/or excipients as described herein. It should also be understood that, in other variations, process 200 may include additional processing steps. In yet other variations, certain steps in process 200 may be omitted.

In one aspect, the present disclosure provides a method for preparing a bilayer tablet, comprising: compacting and milling acetylsalicylic acid, sodium carbonate, and colloidal silicon dioxide to provide granules; combining the granules with acetylsalicylic acid, cornstarch, powdered cellulose, and colloidal silicon dioxide to provide an acetylsalicylic acid blend; combining pseudoephedrine or a pharmaceutically acceptable salt thereof, cornstarch, mannitol, sodium carbonate, microcrystalline cellulose and colloidal silicon dioxide to provide a pseudoephedrine blend; and compressing the acetylsalicylic acid blend and pseudoephedrine blend to form the bilayer tablet.

In step 202, granules comprising acetylsalicylic acid, also referred to herein as an acetylsalicylic acid composite, are prepared. As described previously, the incorporation of the acetylsalicylic acid composite in the acetylsalicylic acid layer confers a number of advantageous pharmacokinetic and stability properties to the resulting bilayer tablet, including for example a fast dissolution rate that provides an enhanced onset of therapeutic action. The granules comprising acetylsalicylic acid contain the active pharmaceutical ingredient in a micronized form that, due to surface area effects, may contribute to the observed enhanced dissolution profile of the bilayer tablet. The inclusion of one or more dissolution aids into the granules further accelerates the rapid dissolution rate of the bilayer tablet. Moreover, the dissolution aids in the granules can serve as a protective, enveloping coating around the micronized acetylsalicylic acid, thereby protecting the acetylsalicylic acid from moisture during downstream processing and in the final tablet.

Acetylsalicylic acid is combined with a dissolution aid and one or more intragranular excipients in a pre-blend mixture, which is compacted and subsequently milled to provide granules comprising acetylsalicylic acid. In some embodiments, prior to being combined with the dissolution aid and intragranular excipients, the acetylsalicylic acid has an average particle size of less than or equal to 50 µm, less than or equal to 40 µm, less than or equal to 30 µm, less than or equal to 20 µm, or less than or equal to 10 µm. In certain embodiments, the acetylsalicylic acid has an average particle size of less than or equal to 40 µm. In some embodiments, prior to being combined with the dissolution aid and intragranular excipients, the acetylsalicylic acid has an average particle size of greater than or equal to 1 µm, greater than or equal to 2 µm, greater than or equal to 5 µm, or greater than or equal to 10 µm. In other embodiments, the acetylsalicylic acid has an average particle size of between 1 µm and 50 µm, between 1 µm and 40 µm, between 1 µm and 30 µm, between 1 µm and 20 µm, between 1 µm and 10 µm, between 2 µm and 50 µm, between 2 µm and 40 µm, between 2 µm and 30 µm, between 2 µm and 20 µm, between 2 µm and 10 µm, between 5 µm and 50 µm, between 5 µm and 40 µm, between 5 µm and 30 µm, between 5 µm and 20 µm, between 5 µm and 10 µm, between 10 µm and 50 µm, between 10 µm and 40 µm, between 10 µm and 30 µm, between 10 µm and 20 µm, between 10 µm and 50 µm, between 20 µm and 40 µm, between 20 µm and 30 µm, between 30 µm and 50 µm, between 30 µm and 40 µm, or between 40 µm and 50 µm.

In some embodiments, the method comprises compacting and milling acetylsalicylic acid, sodium carbonate (or other suitable dissolution aid), and colloidal silicon dioxide to provide granules. In some embodiments, acetylsalicylic acid, sodium carbonate, and colloidal silicon dioxide are compacted by roller compaction. In certain embodiments, acetylsalicylic acid, sodium carbonate, and colloidal silicon dioxide are compacted by roller compaction with variable roller size, roller speeds, roller gaps, and/or roller pressures.

In some embodiments of the foregoing, acetylsalicylic acid, sodium carbonate, and colloidal silicon dioxide are compacted by roller compaction with a roller speed of at least 5 rpm, at least 6 rpm, at least 7 rpm, at least 8 rpm, or at least 9 rpm. In other embodiments, acetylsalicylic acid, sodium carbonate, and colloidal silicon dioxide are compacted by roller compaction with a roller speed of less than or equal to 20 rpm, less than or equal to 17 rpm, less than or equal to 15 rpm, or less than or equal to 12 rpm.

In other embodiments, which may be combined with any of the preceding embodiments, acetylsalicylic acid, sodium carbonate, and colloidal silicon dioxide are compacted by roller compaction with a roller gap of at least 1 mm, at least 1.2 mm, at least 1.4 mm, or at least 1.6 mm. In still other embodiments, acetylsalicylic acid, sodium carbonate, and colloidal silicon dioxide are compacted by roller compaction with a roller gap of less than or equal to 3 mm, less than or equal to 2.8 mm, less than or equal to 2.6 mm, or less than or equal to 2.4 mm.

In some embodiments, which may be combined with any of the foregoing embodiments, acetylsalicylic acid, sodium carbonate, and colloidal silicon dioxide are compacted by roller compaction with a roller pressure of at least 10 bar, at least 12 bar, at least 15 bar, at least 17 bar or at least 20 bar. In other embodiments, acetylsalicylic acid, sodium carbonate, and colloidal silicon dioxide are compacted by roller compaction with a roller pressure of less than or equal to 50 bar, less than or equal to 45 bar, less than or equal to 40 bar, or less than or equal to 35 bar.

Following compaction, the resulting compacted material (acetylsalicylic acid, sodium carbonate or other dissolution aid, and colloidal silicon dioxide) are milled to provide granules. The milling step may include but is not limited to dry milling techniques, such as ball milling, air-jet milling, or techniques employing mechanical mills (such as hammer mills or conical mills). In some embodiments, the compacted material is milled with a milling speed of at least 50 rpm, at least 75 rpm, or at least 100 rpm. In other embodiments, the compacted material is milled with a milling speed of less than or equal to 150 rpm, less than or equal to 125 rpm, or less than or equal to 110 rpm.

It should be recognized that the parameters of the compaction and/or milling steps described above as well as the residence time for the milling step may be modified accordingly to achieve suitable particle sizes of the resulting granules. Furthermore, it should be recognized that the parameters employed for the compaction and milling steps may vary depending on the compacting or milling equipment utilized. Accordingly, in some embodiments, after the compacting and milling steps, the resulting acetylsalicylic acid composite, or granules, may be characterized by their particle size distribution and/or other particle size properties.

In some embodiments, the granules have a particle size distribution wherein at least 5% w/w, at least 10% w/w, or at least 15% w/w of the granules out of the total granule weight has a particle size of less than 150 µm. In other embodiments, the granules have a particle size distribution wherein less than or equal to 30% w/w, less than or equal to 25% w/w less than or equal to 20% w/w of the granules out of the total granule weight has a particle size of less than 150 µm.

In some embodiments, the granules have a particle size distribution wherein at least 50% w/w, at least 55% w/w, or at least 60% w/w of the granules out of the total granule weight has a particle size of greater than 400 µm. In other embodiments, the granules have a particle size distribution wherein less than or equal to 80% w/w, less than or equal to 75% w/w less than or equal to 70% w/w of the granules out of the total granule weight has a particle size of greater than 400 µm.

In some embodiments, the granules have a particle size distribution wherein at least 10% w/w, at least 15% w/w, or at least 20% w/w of the granules out of the total granule weight have a particle size between 150 µm and 400 µm. In other embodiments, the granules have a particle size distribution wherein less than or equal to 40% w/w, less than or equal to 35% w/w, less than or equal to 30% w/w, or less than or equal to 25% w/w of the granules out of the total granule weight have a particle size between 150 µm and 400 µm.

In still other embodiments, the granules have a particle size distribution wherein at least 5% w/w, at least 10% w/w, or at least 15% w/w of the granules out of the total granule weight has a particle size of less than or equal to 150 µm and less than or equal to 80% w/w, less than or equal to 75% w/w less than or equal to 70% w/w of the granules out of the total granule weight has a particle size of greater than or equal to 400 µm. In yet other embodiments, the granules have a particle size distribution wherein less than or equal to 30% w/w, less than or equal to 25% w/w less than or equal to 20% w/w of the granules out of the total granule weight has a particle size of less than or equal to 150 µm and at least 50% w/w, at least 55% w/w, or at least 60% w/w of the granules out of the total granule weight has a particle size of greater than or equal to 400 µm.

In certain embodiments, the granules have a particle size distribution wherein between 5% w/w and 30% w/w, between 10% w/w and 30% w/w, between 15% w/w and 30% w/w, between 5% w/w and 25% w/w, between 10% w/w and 25% w/w, between 15% w/w and 25% w/w, between 5% w/w and 20% w/w, between 10% w/w and 20% w/w, or between 15% w/w and 20% w/w of the granules out of the total granule weight have a particle size of less than 150 µm; and wherein between 50% w/w and 80% w/w, between 55% w/w and 80% w/w, between 60% w/w and 80% w/w, between 50% w/w and 75% w/w, between 55% w/w and 75% w/w, between 60% w/w and 75% w/w, between 50% w/w and 70% w/w, between 55% w/w and 70% w/w, or between 60% w/w and 70% w/w, of the granules out of the total granule weight have a particle size of greater than 400 µm. In certain embodiments, the granules have a particle size distribution wherein between 5% w/w and 30% w/w of the granules out of the total granule weight have a particle size of less than 150 µm and wherein between 50% w/w and 80% w/w of the granules out of the total granule weight have a particle size of greater than 400 µm.

In still further embodiments, the granules produced by the milling step may be further sieved to provide granules having a particular particle size distribution. In some embodiments, the method further comprises sieving the granules prior to combining the granules with extragranular components.

In some embodiments, the granules produced by the milling step are sieved to provide granules having a particle size distribution wherein at least 5% w/w, at least 10% w/w, or at least 15% w/w of the total granule weight has a particle size of less than or equal to 150 µm. In other embodiments, the granules have a particle size distribution wherein less than or equal to 30% w/w, less than or equal to 25% w/w less than or equal to 20% w/w of the total granule weight has a particle size of less than or equal to 150 µm. In some embodiments, the granules produced by the milling step are sieved to provide granules having a particle size distribution wherein at least 50% w/w, at least 60% w/w, or at least 70% w/w of the total granule weight has a particle size of greater than or equal to 400 µm. In other embodiments, the granules produced by the milling step are sieved to provide granules having a particle size distribution wherein less than or equal to 95% w/w, less than or equal to 90% w/w less than or equal to 85% w/w of the total granule weight has a particle size of greater than or equal to 400 µm.

In some embodiments, the granules produced by the milling step are sieved to provide granules having a particle size distribution wherein at least 5% w/w, at least 10% w/w, or at least 15% w/w of the granules out of the total granule weight has a particle size of less than 150 µm. In other embodiments, the granules produced by the milling step are sieved to provide granules having a particle size distribution wherein less than or equal to 30% w/w, less than or equal to 25% w/w less than or equal to 20% w/w of the granules out of the total granule weight has a particle size of less than 150 µm.

In some embodiments, the granules produced by the milling step are sieved to provide granules having a particle size distribution wherein at least 50% w/w, at least 55% w/w, or at least 60% w/w of the granules out of the total granule weight has a particle size of greater than 400 µm. In other embodiments, the granules produced by the milling step are sieved to provide granules having a particle size distribution wherein less than or equal to 80% w/w, less than or equal to 75% w/w less than or equal to 70% w/w of the granules out of the total granule weight has a particle size of greater than 400 µm.

In some embodiments, the granules produced by the milling step are sieved to provide granules having a particle size distribution wherein at least 10% w/w, at least 15% w/w, or at least 20% w/w of the granules out of the total granule weight have a particle size between 150 µm and 400 µm. In other embodiments, the granules produced by the milling step are sieved to provide granules having a particle size distribution wherein less than or equal to 40% w/w, less than or equal to 35% w/w, less than or equal to 30% w/w, or less than or equal to 25% w/w of the granules out of the total granule weight have a particle size between 150 µm and 400 µm.

In still other embodiments, the granules produced by the milling step are sieved to provide granules having a particle size distribution wherein at least 5% w/w, at least 10% w/w, or at least 15% w/w of the granules out of the total granule weight has a particle size of less than or equal to 150 µm and less than or equal to 80% w/w, less than or equal to 75% w/w less than or equal to 70% w/w of the granules out of the total granule weight has a particle size of greater than or equal to 400 µm. In yet other embodiments, the granules produced by the milling step are sieved to provide granules having a particle size distribution wherein less than or equal to 30% w/w, less than or equal to 25% w/w less than or equal to 20% w/w of the granules out of the total granule weight has a particle size of less than or equal to 150 µm and at least 50% w/w, at least 55% w/w, or at least 60% w/w of the granules out of the total granule weight has a particle size of greater than or equal to 400 µm.

In certain embodiments, the granules produced by the milling step are sieved to provide granules having a particle size distribution wherein between 5% w/w and 30% w/w, between 10% w/w and 30% w/w, between 15% w/w and 30% w/w, between 5% w/w and 25% w/w, between 10% w/w and 25% w/w, between 15% w/w and 25% w/w, between 5% w/w and 20% w/w, between 10% w/w and 20% w/w, or between 15% w/w and 20% w/w of the granules out of the total granule weight have a particle size of less than 150 µm; and wherein between 50% w/w and 80% w/w, between 55% w/w and 80% w/w, between 60% w/w and 80% w/w, between 50% w/w and 75% w/w, between 55% w/w and 75% w/w, between 60% w/w and 75% w/w, between 50% w/w and 70% w/w, between 55% w/w and 70% w/w, or between 60% w/w and 70% w/w, of the granules out of the total granule weight have a particle size of greater than 400 µm. In certain embodiments, the granules produced by the milling step are sieved to provide granules having a particle size distribution wherein between 5% w/w and 30% w/w of the granules out of the total granule weight have a particle size of less than 150 µm and wherein between 50% w/w and 80% w/w of the granules out of the total granule weight have a particle size of greater than 400 µm.

With reference to step 204, the method comprises combining the granules with additional acetylsalicylic acid and one or more extragranular excipients. In some embodiments, the method comprises combining the granules with acetylsalicylic acid, cornstarch, powdered cellulose, and colloidal silicon dioxide to provide an acetylsalicylic acid blend. In some embodiments, the additional extragranular acetylsalicylic acid may have the same or different particle size properties as the acetylsalicylic acid used in the preparation of the granules. In some embodiments, the acetylsalicylic acid has an average particle size of less than or equal to 50 µm, less than or equal to 40 µm, less than or equal to 30 µm, less than or equal to 20 µm, or less than or equal to 10 µm. In certain embodiments, the acetylsalicylic acid has an average particle size of less than or equal to 40 µm. In other embodiments, the additional acetylsalicylic acid has an average particle size of greater than or equal to 1 µm, greater than or equal to 2 µm, greater than or equal to 5 µm, or greater than or equal to 10 µm. In other embodiments, the acetylsalicylic acid has an average particle size of between 1 µm and 50 µm, between 1 µm and 40 µm, between 1 µm and 30 µm, between 1 µm and 20 µm, between 1 µm and 10 µm, between 2 µm and 50 µm, between 2 µm and 40 µm, between 2 µm and 30 µm, between 2 µm and 20 µm, between 2 µm and 10 µm, between 5 µm and 50 µm, between 5 µm and 40 µm, between 5 µm and 30 µm, between 5 µm and 20 µm, between 5 µm and 10 µm, between 10 µm and 50 µm, between 10 µm and 40 µm, between 10 µm and 30 µm, between 10 µm and 20 µm, between 20 µm and 50 µm, between 20 µm and 40 µm, between 20 µm and 30 µm, between 30 µm and 50 µm, between 30 µm and 40 µm, or between 40 µm and 50 µm.

Acetylsalicylic acid is susceptible to hydrolytic degradation pathways to form various inactive and/or less stable byproducts, such as free salicylic acid. Minimization of hydrolysis may be achieved by drying the acetylsalicylic acid blend prior to passing the acetylsalicylic acid blend to the tablet press for compression. In some embodiments, prior to compressing, the method comprises drying the acetylsalicylic acid blend prior to compressing. In certain embodiments, the method comprises drying the acetylsalicylic acid blend to a moisture content or water activity below a certain threshold level. Water activity may be determined as described in USP42-NF37 Chapters <922> Water Activity and <1112> Application Of Water Activity Determination To Nonsterile Pharmaceutical Products. In some embodiments, the method comprises drying the acetylsalicylic acid blend to a water activity of less than or equal to 0.4, less than or equal to 0.3, less than or equal to 0.2, less than or equal to 0.1, or less than or equal to 0.08. In some embodiments, the method comprises drying the acetylsalicylic acid blend to a water activity of between 0.01 and 0.3, between 0.02 and 0.2, or between 0.05 and 0.1.

With reference to step 206, the method comprises combining pseudoephedrine or a pharmaceutically acceptable salt thereof, such as pseudoephedrine hydrochloride, with one or more excipients, including for example, cornstarch, mannitol, sodium carbonate, microcrystalline cellulose and colloidal silicon dioxide, to provide a pseudoephedrine blend.

With further reference to FIG. 2, in step 208, external lubricants may be added to the tablet press or other tableting equipment prior to forming the bilayer tablet with the two blends. The use of external lubricants may facilitate the ejection of the final tablet by reducing sticking of material to the tablet press. In still further embodiments of the foregoing, the method comprises optionally applying one or more external lubricants to the tablet press prior to compressing. In some embodiments, the one or more external lubricants comprise hypromellose, zinc stearate, carnauba wax, or any combinations thereof.

Depending upon the tablet press utilized, the compression of the two blends in step 210 to form the bilayer tablet may be carried out in a single compression step or in a two-step process comprising first (pre-)compressing one of the blends to form one layer, subsequently loading the remaining blend into the press with the already prepared layer, and compressing the remaining blend and prepared layer to form the bilayer tablet. It should be recognized that, in instances wherein the two-step process for tableting is utilized, the sequence of compression may be ordered with either the acetylsalicylic acid blend or pseudoephedrine blend may be subjected to the pre-compression.

In some embodiments wherein the acetylsalicylic acid blend and pseudoephedrine blend are compressed in a single compression step, the acetylsalicylic acid blend and pseudoephedrine blend are compressed at a compression force of at least 1 kN, at least 2 kN, at least 3 kN, at least 4 kN, at least 5 kN, at least 10 kN, at least 15 kN, at least 20 kN, or at least 25 kN. In other embodiments, the acetylsalicylic acid blend and pseudoephedrine blend are compressed at a compression force of less than or equal to 45 kN, less than or equal to 40 kN, less than or equal to 35 kN, less than or equal to 30 kN, less than or equal to 25 kN, or less than or equal to 20 kN. In certain embodiments, the acetylsalicylic acid blend and the pseudoephedrine blend are compressed at a compression force of between 5 kN and 45 kN, between 5 kN and 40 kN, between 5 kN and 35 kN, between 5 kN and 30 kN, between 5 kN and 25 kN, between 5 kN and 20 kN, between 5 kN and 15 kN, between 5 kN and 10 kN, between 10 kN and 45 kN, between 10 kN and 40 kN, between 10 kN and 35 kN, between 10 kN and 30 kN, between 10 kN and 25 kN, between 10 kN and 20 kN, between 10 kN and 15 kN, between 15 kN and 45 kN, between 15 kN and 40 kN, between 15 kN and 35 kN, between 15 kN and 30 kN, between 15 kN and 25 kN, between 15 kN and 20 kN, between 20 kN and 45 kN, between 20 kN and 40 kN, between 20 kN and 35 kN, between 20 kN and 30 kN, between 20 kN and 25 kN, between 25 kN and 45 kN, between 25 kN and 40 kN, between 25 kN and 35 kN, between 25 kN and 30 kN, between 30 kN and 45 kN, between 30 kN and 40 kN, between 30 kN and 35 kN, between 35 kN and 45 kN, between 35 kN and 40 kN, or between 40 kN and 45 kN.

In some embodiments wherein the acetylsalicylic acid blend and the pseudoephedrine blend are compressed in a two-step process, the acetylsalicylic acid blend or pseudoephedrine blend may be compressed at a first compression force to form a first layer, followed by compression of the pseudoephedrine blend or acetylsalicylic acid blend on top of the first layer at a second compression force to form the bilayer tablet.

In some embodiments, the method comprises compressing the acetylsalicylic acid blend to provide an acetylsalicylic acid layer; and compressing the pseudoephedrine blend on top of the acetylsalicylic acid layer to provide the bilayer tablet. In certain embodiments, the method comprises compressing the acetylsalicylic acid blend to provide an acetylsalicylic acid layer at a first compression force; and compressing the pseudoephedrine blend on top of the acetylsalicylic acid layer at a second compression force to provide the bilayer tablet. In other embodiments, the method comprises compressing the pseudoephedrine blend to provide a pseudoephedrine layer; and compressing the acetylsalicylic acid blend on top of the pseudoephedrine layer to provide the bilayer tablet. In certain other embodiments, the method comprises compressing the pseudoephedrine blend at a first compression force to provide a pseudoephedrine layer; and compressing the acetylsalicylic acid blend on top of the pseudoephedrine layer at a second compression force to provide the bilayer tablet.

In some embodiments, the first compression force is at least 1 kN, at least 2 kN, at least 3 kN, at least 4 kN, at least 5 kN, at least 10 kN, at least 15 kN, at least 20 kN, or at least 25 kN. In other embodiments, the first compression force is less than or equal to 45 kN, less than or equal to 40 kN, less than or equal to 35 kN, less than or equal to 30 kN, less than or equal to 25 kN, or less than or equal to 20 kN. In some embodiments, the second compression force is at least 5 kN, at least 10 kN, at least 15 kN, at least 20 kN, or at least 25 kN. In other embodiments, the second compression force is less than or equal to 45 kN, less than or equal to 40 kN, less than or equal to 35 kN, less than or equal to 30 kN, less than or equal to 25 kN, or less than or equal to 20 kN.

In some embodiments, the first compression force and the second compression force are the same. In other embodiments, the first compression force and the second compression force are different. In still further embodiments, the first compression force is less than or equal to the second compression force.

Methods of Use and Articles of Manufacture

The bilayer tablets as described herein may be suitable for use in the treatment of or provision of relief from symptoms associated with the common cold and/or flu, including nasal congestion experienced in conjunction with fever and/or pain.

In one aspect, the present disclosure provides methods for using the bilayer tablets of the present disclosure.

In some embodiments, provided herein is a method for treating nasal/sinus congestion (rhinosinusitis) with pain and fever associated with the common cold and/or flu-like symptoms in a subject in need thereof, comprising administering a bilayer tablet as described herein to the subject.

As described herein a subject may include but is not limited to a mammal, or more particularly a human. In certain embodiments, provided herein is a method for treating nasal/sinus congestion (rhinosinusitis) with pain and fever associated with the common cold and/or flu-like symptoms in a human in need thereof, comprising administering a bilayer tablet as described herein to the human.

In certain embodiments of the foregoing methods, the bilayer tablet is administered orally. In still other embodiments, the bilayer tablet is formulated for oral administration.

In other aspects, provided is an article of manufacture, such as a container comprising a bilayer tablet as described herein, and a label containing instructions for use of the bilayer tablet. In some embodiments, provided herein is a package comprising a bilayer tablet as described herein. In certain embodiments, the package further comprises a desiccant. In still further embodiments, the package further comprises a package insert or a package label containing instructions for use of the bilayer tablet.

In yet other aspects, provided is a kit comprising a bilayer tablet as described herein; and instructions for use of such a bilayer tablet.

In certain embodiments of the foregoing aspects, the instructions for use are instructions for use of the bilayer tablet in treatment of nasal/sinus congestion with pain and fever associated with the common cold and/or flu-like symptoms.

ENUMERATED EMBODIMENTS

The following enumerated embodiments are representative of some aspects of the disclosure.

1. A bilayer tablet, comprising:
    an acetylsalicylic acid layer, comprising:
        granules, wherein the granules comprise intragranular acetylsalicylic acid, intragranular sodium carbonate, and one or more intragranular excipients;
        extragranular acetylsalicylic acid; and
        one or more extragranular excipients; and
    a pseudoephedrine layer, comprising:
        pseudoephedrine or a pharmaceutically acceptable salt thereof;
        sodium carbonate; and
        one or more excipients;
    wherein 10-50% w/w of the total acetylsalicylic acid present in the tablet is intragranular acetylsalicylic acid, and
    wherein the tablet has a weight ratio of the acetylsalicylic acid to sodium carbonate of between 1:1 and 5:1.

2. The tablet of embodiment 1, wherein the tablet has a weight ratio of acetylsalicylic acid to sodium carbonate between 2:1 and 4:1.

3. The tablet of embodiment 1 or embodiment 2, wherein 10-50% w/w of the total sodium carbonate present in the tablet is intragranular sodium carbonate.

4. The tablet of any one of embodiments 1 to 3, wherein 20-40% w/w of the total acetylsalicylic acid present is intragranular acetylsalicylic acid.

5. The tablet of any one of embodiments 1 to 4, wherein 20-40% w/w of the total sodium carbonate present in the tablet is present in the acetylsalicylic acid layer.

6. The tablet of any one of embodiments 1 to 5, wherein the weight percentage of intragranular acetylsalicylic acid out of the total acetylsalicylic acid present is equal to the weight percentage of the intragranular sodium carbonate out of the total sodium carbonate present in the tablet.
7. The tablet of any one of embodiments 1 to 6, comprising between 250 mg and 1000 mg acetylsalicylic acid.
8. The tablet of any one of embodiments 1 to 7, comprising between 15 mg and 60 mg pseudoephedrine or a pharmaceutically acceptable salt thereof.
9. The tablet of any one of embodiments 1 to 8, wherein the pseudoephedrine or a pharmaceutically acceptable salt thereof is pseudoephedrine hydrochloride.
10. The tablet of any one of embodiments 1 to 9, wherein the one or more intragranular excipients in the granules comprises colloidal silicon dioxide.
11. The tablet of any one of embodiments 1 to 10, wherein the one or more extragranular excipients in the acetylsalicylic acid layer comprises colloidal silicon dioxide, cornstarch, and cellulose.
12. The tablet of any one of embodiments 1 to 11, wherein the one or more excipients in the pseudoephedrine layer comprises mannitol, microcrystalline cellulose, cornstarch, and colloidal silicon dioxide.
13. The tablet of any one of embodiments 1 to 12, further comprising a coating.
14. The tablet of any one of embodiments 1 to 13, wherein the tablet comprises less than or equal to 4% w/w salicylic acid of the initial acetylsalicylic acid content after storage at 50° C. and 65% relative humidity for at least 10 days.
15. The tablet of any one of embodiments 1 to 14, wherein the tablet comprises less than or equal to 4% w/w salicylic acid of the initial acetylsalicylic acid content after storage at 40° C. and 75% relative humidity for at least 1 month.
16. The tablet of any one of embodiments 1 to 15, wherein the tablet comprises at least 95% acetylsalicylic acid of the initial acetylsalicylic acid content after storage at 40° C. and 75% relative humidity for at least 1 month.
17. The tablet of any one of embodiments 1 to 16, wherein the tablet has a dissolution profile wherein at least 85% acetylsalicylic acid and at least 85% pseudoephedrine are dissolved at 10 minutes as determined by USP Dissolution Test (Apparatus 1) in 50 mM sodium acetate buffer at pH 4.5 at 37±0.5° C.
18. A method for preparing a bilayer tablet according to any one of embodiments 1 to 17, comprising:
  compacting and milling acetylsalicylic acid, sodium carbonate, and colloidal silicon dioxide to provide granules;
  combining the granules with acetylsalicylic acid, cornstarch, powdered cellulose, and colloidal silicon dioxide to provide an acetylsalicylic acid blend;
  combining pseudoephedrine or a pharmaceutically acceptable salt thereof, cornstarch, mannitol, sodium carbonate, microcrystalline cellulose and colloidal silicon dioxide to provide a pseudoephedrine blend; and
  compressing the acetylsalicylic acid blend and pseudoephedrine blend to form the bilayer tablet.
19. The method of embodiment 18, comprising compacting the acetylsalicylic acid, sodium carbonate, and colloidal silicon dioxide by roller compaction.
20. The method of embodiment 18 or 19, wherein the granules have a particle size distribution wherein between 5% w/w and 30% w/w of the granules out of the total granule weight have a particle size of less than 150 µm, and between 50% w/w and 80% w/w of the granules out of the total granule weight have a particle size of greater than 400 µm.
21. The method of any one of embodiments 18 to 20, further comprising drying the acetylsalicylic acid blend prior to compressing.
22. The method of embodiment 21, comprising drying the acetylsalicylic acid blend to a water activity of less than or equal to 0.2.
23. The method of any one of embodiments 18 to 22, wherein the pseudoephedrine or a pharmaceutically acceptable salt thereof is pseudoephedrine hydrochloride.
24. The method of any one of embodiments 18 to 23, comprising compressing the acetylsalicylic acid blend and pseudoephedrine blend at a compression force between 1 kN and 30 kN.
25. The method of any one of embodiments 18 to 24, comprising compressing the acetylsalicylic acid blend and pseudoephedrine blend at a compression force between 10 kN and 20 kN.
26. The method of any one of embodiments 18 to 23, wherein compressing the acetylsalicylic acid blend and pseudoephedrine blend to form the bilayer tablet comprises:
  compressing the acetylsalicylic acid blend at a first compression force to provide an acetylsalicylic acid layer; and
  compressing the pseudoephedrine blend on top of the acetylsalicylic acid layer at a second compression force to form the bilayer tablet.
27. The method of any one of embodiments 18 to 23, wherein compressing the compressing the acetylsalicylic acid blend and pseudoephedrine blend to form the bilayer tablet comprises:
  compressing the pseudoephedrine blend at a first compression force to provide a pseudoephedrine layer; and
  compressing the acetylsalicylic acid blend on top of the pseudoephedrine layer at a second compression force to form the bilayer tablet.
28. The method of embodiment 26 or embodiment 27, wherein the first compression force is between 1 kN and 30 kN and the second compression force is between 5 kN and 30 kN.
29. The method of any one of embodiments 18 to 28, further comprising coating the tablet.
30. A method for treating nasal congestion and pain or fever a in a human in need thereof, comprising administering a bilayer tablet according to any one of embodiments 1 to 17 to the human.
31. A package comprising a bilayer tablet according to any one of embodiments 1 to 17.
32. The package according to embodiment 31, further comprising a desiccant.

EXAMPLES

The presently disclosed subject matter will be better understood by reference to the following Examples, which are provided as exemplary of the invention, and not by way of limitation.

Example 1: Preparation of a Bilayer Tablet Comprising Acetylsalicylic Acid and Pseudoephedrine HCl The present example describes a method for preparing a bilayer tablet as described herein. FIG. 1 depicts a schematic of the bilayer tablet produced in this example. Table 1 below details the ingredient list for the separate layers of the bilayer tablet.

TABLE 1

| | Ingredient Function | % w/w | mg/tablet |
|---|---|---|---|
| ACETYLSALICYLIC ACID-LAYER I | | | |
| 1 Acetylsalicylic acid Granulation | | 32.16 | 200.4 |
| 1a Acetylsalicylic acid | Active | 24.07 | 150.0 |
| 1b Sodium Carbonate | Diluent | 7.94 | 49.5 |
| 1c Colloidal Silicon Dioxide | Flow Aid | 0.14 | 0.9 |
| 2 Acetylsalicylic acid (0-180), USP | Active | 56.17 | 350.0 |
| 3 Powdered Cellulose, NF | Binder | 5.62 | 35.0 |
| 4 Cornstarch, NF | Disintegrant | 5.62 | 35.0 |
| 5 Colloidal Silicon Dioxide, NF | Flow Aid | 0.43 | 2.7 |
| Acetylsalicylic acid Layer Sub-total | | 100.00 | 623.1 |
| PSEUDOEPHEDRINE HCL-LAYER II | | | |
| 6 Pseudoephedrine HCl, USP | Active | 8.21 | 30.0 |
| 7 Mannitol, USP | Filler/Diluent | 32.50 | 118.8 |
| 8 Sodium Carbonate anhydrous, USP | Diluent | 31.60 | 115.5 |
| 9 Microcrystalline Cellulose, NF | Binder | 13.68 | 50.0 |
| 10 Cornstarch, NF | Disintegrant | 13.68 | 50.0 |
| 11 Colloidal Silicon Dioxide, NF | Flow Aid | 0.33 | 1.2 |
| Pseudoephedrine Layer Sub-total | | 100.00 | 365.5 |
| Bilayer Tablet | | | |
| Acetylsalicylic acid Layer (Layer I) | | 63.03 | 623.1 |
| Pseudoephedrine HCl Layer (Layer II) | | 36.97 | 365.5 |
| 12 Dry Coating Powder Blend (Hypromellose/Zinc Stearate/Carnauba Wax Blend, 50%/40%/10% w/w)* | External Lubrication Blend | Trace | Trace |
| Bilayer Tablet Total | | 100.00 | 988.6 |

Acetylsalicylic acid Layer. As provided in the present disclosure, the bilayer tablet comprising an acetylsalicylic acid layer contains acetylsalicylic acid in granulated and non-granulated forms. Granulated acetylsalicylic acid was prepared by combining acetylsalicylic acid with sodium carbonate and colloidal silicon dioxide. Acetylsalicylic acid, sodium and colloidal silicon dioxide were combined in the mass proportions shown in Table 1 above for ingredients 1a, 1b and 1c, passed through roller compactors (at roller speed of 9 rpm, a roller pressure of 20-35 bar, and a roller gap of 1.4-3.0 mm) to provide compressed material in the form of rectangular ribbons, and the resulting compacted ribbons milled (at a mill speed of 107 rpm).

The acetylsalicylic acid granules were then combined with additional powdered acetylsalicylic acid and extra-granular excipients (powdered cellulose, cornstarch and colloidal silicon dioxide) at the mass proportions shown in Table 1 for ingredients 2-5. The resulting acetylsalicylic acid blend containing the granulated acetylsalicylic acid and powdered acetylsalicylic acid was dried to a moisture content of 8% wt. and held in storage until the pseudoephedrine blend was prepared.

Pseudoephedrine Layer. Pseudoephedrine hydrochloride was combined with mannitol, anhydrous sodium carbonate, microcrystalline cellulose, cornstarch and colloidal silicon dioxide in the mass proportions indicated in Table 1 above to provide a pseudoephedrine blend.

Tableting. Following preparation of the acetylsalicylic acid and pseudoephedrine blends, the two blends were fed into a bilayer tablet press sequentially for compression. The tablet press was pre-treated with an application of external lubrication (hypromellose/zinc stearate/carnauba wax blend, 50%/40%/10% w/w) to reduce material sticking and aid ejection of the tablets from the press. The acetylsalicylic acid blend was fed into the tablet first and compressed at a compression force of 3 kN to provide the acetylsalicylic acid layer. The pseudoephedrine blend was then added to the acetylsalicylic acid layer and the pseudoephedrine blend was compressed at a compression force of 26 kN to provide the pseudoephedrine layer and acetylsalicylic acid layer in the final bilayer tablet form.

Example 2: Ratio of Granulated to Non-Granulated Acetylsalicylic Acid in Acetylsalicylic Acid Layer In the present example, the effect of varying ratios of granulated acetylsalicylic acid (roller-compacted, RC) to non-granulated acetylsalicylic acid (powdered, direct compression, DC) on the stability of the acetylsalicylic acid layer to degradation was evaluated. Six separate acetylsalicylic acid monolayer tablet formulations having one of six ratios of granulated to non-granulated (0:100, 10:90, 20:80, 30:70, 40:60 and 50:50) were prepared largely in accordance with the protocol described in Example 1 above.

In each sample formulation, the ratio of total acetylsalicylic acid to total sodium carbonate in the bilayer tablet was maintained at 3:1; the ratio of acetylsalicylic acid present in the granules (if present) to the sodium carbonate present in the granules was also maintained at 3:1, with the remainder of sodium carbonate included in the second layer of pseudoephedrine.

Approximately 10 individual tablets of each formulation ratio were subjected to accelerated stability conditions (storage at 50° C. at a 65% relative humidity for 20 days) in order to evaluate the stability of each tablet to degradation of acetylsalicylic acid into salicylic acid (or "free salicylic acid", FSA) and other degradation products. Following storage, the quantity of free salicylic acid formed and total acetylsalicylic acid-derived degradation products (including salicylic acid) were determined by HPLC analysis.

HPLC Analysis. The concentrations of acetylsalicylic acid (ASA) and pseudoephedrine hydrochloride (PSEH) present in the tablets after storage were determined by HPLC analysis, as calibrated an HPLC chromatogram of a known sample of acetylsalicylic acid and pseudoephedrine hydrochloride as a standard solution. After storage, HPLC injection samples were prepared by dissolving the tablets in a solution of 0.01N sulfuric acid:acetonitrile 80:20, v/v. Aliquots of the sample solutions were injected into an HPLC column under the following parameters and conditions: injection volume 15 μL; column: Waters XSelect®, HSS PFP 2.5 μm, 100 Å, length: 100 mm, ID: 4.6 mm; column temperature 40±2° C.; Mobile Phase A: 50 mM $NaClO_4$, pH 2.5, Mobile Phase B: ACN:MeOH, 60:40 v/v; UV detection wavelengths: 257 nm for acetylsalicylic acid and 214 nm for pseudoephedrine hydrochloride.

The determination of the concentrations of two major acetylsalicylic acid degradation products—free salicylic acid (FSA) and acetylsalicylsalicylic acid (ASSA)—were carried out as measured against the response of a known sample of acetylsalicylsalicylic acid (ASSA) (detection wavelength 257 nm). The quantitation of acetylsalicylic acid-derived degradation products were measured as calibrated against the response of the known sample of acetylsalicylsalicylic acid, with the application of relative response factors for each degradation product [relative response factor as compared to ASSA, for: free salicylic acid (FSA) 0.329× factor]. All pseudoephedrine-derived degradation products were measured as calibrated against the response known sample of pseudoephedrine hydrochloride, with the application of relative response factors for each degradation product [relative response factor as compared to PSEH, for: N-acetyl pseudoephedrine (PSEH-N ester) 2.207×; O-acetyl pseudoephedrine (PSEH-O ester) 0.883×; and N,O-acetyl pseudoephedrine (PSEH diester) 1.834×].

Figure 3:
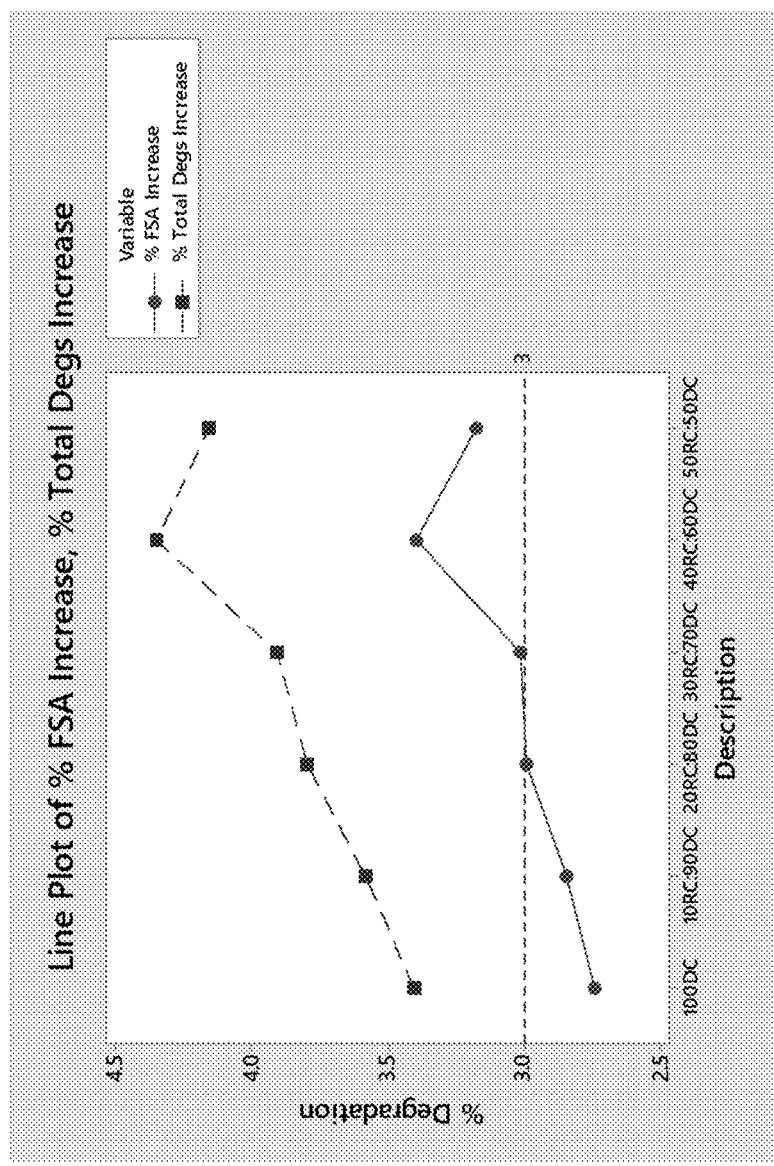
FIG. 3 depicts plots of the percentage of degradation products (free salicylic acid alone ("FSA") and total acetylsalicylic acid-derived degradation products ("Total Degs") including free salicylic acid) as a function of the ratio of granulated (roller-compacted, "RC") to non-granulated (direct compression, "DC") acetylsalicylic acid.

As shown in FIG. 3, increased quantities of granulated acetylsalicylic acid resulted in increasing quantities of free salicylic acid and other degradation products.

Example 3: Bilayer Tablet Dissolution Profile Testing

The present example describes experiments to evaluate the dissolution profile of bilayer tablets formed with varying ratios of granulated acetylsalicylic acid to non-granulated acetylsalicylic acid within the acetylsalicylic acid layer as well as differing distributions of sodium carbonate throughout the acetylsalicylic acid and pseudoephedrine layers.

Six separate bilayer tablet formulations were prepared as described Example 1 above with the distributions of sodium carbonate and ratios of granulated acetylsalicylic acid (intragranular, "INTRA") to non-granulated acetylsalicylic acid (extragranular, "EXTRA") as shown in Table 2 below. All six formulations contained a fixed quantity of 500 mg acetylsalicylic acid (ASA), 30 mg pseudoephedrine hydrochloride (PSEH), and 165 mg sodium carbonate ($Na_2CO_3$), in which all sodium carbonate in the acetylsalicylic acid layer (Layer I) was contained within the granulated acetylsalicylic acid.

TABLE 2

| | Acetylsalicylic acid | | | $Na_2CO_3$ | | |
|---|---|---|---|---|---|---|
| | | | | ASA Layer | PSEH Layer | |
| Sample # | INTRA (mg) | EXTRA (mg) | Intra:Extra Ratio | (I) (mg) | (II) (mg) | Layer I:Layer II Ratio |
| 1 | 150 | 350 | 30:70 | 165 | 0 | 100:0 |
| 2 | 150 | 350 | 30:70 | 165 | 0 | 100:0 |
| 3 | 50 | 450 | 10:90 | 165 | 0 | 100:0 |
| 4 | 150 | 350 | 30:70 | 49.5 | 115.5 | 30:70 |
| 5 | 50 | 450 | 10:90 | 82.5 | 82.5 | 50:50 |
| 6 | 150 | 350 | 30:70 | 82.5 | 82.5 | 50:50 |

The dissolution profiles of each active ingredient in the bilayer tablet—the acetylsalicylic acid and pseudoephedrine hydrochloride—were evaluated in a dual dissolution test performed as described below. In brief, a single bilayer tablet is placed in a basket apparatus (Apparatus 1) containing 50 mM sodium acetate buffer of pH 4.5 (500 mL, equilibrated to 37±0.5° C.), at rotation speed of 50 rpm. Aliquots of the dissolution medium were taken at 2 minutes, 8 minutes, 15 minutes and 30 minutes. The quantities of each of the acetylsalicylic acid and pseudoephedrine hydrochloride dissolved in the dissolution medium were determined by UV absorption spectrometry at 257 nm and 214 nm, respectively. The dissolution measurements were taken for three bilayer tablets (n=3) for each bilayer tablet formulation.

Table 3 and Table 4 below respectively show the observed average percentages of acetylsalicylic acid dissolved and pseudoephedrine hydrochloride dissolved at each time point.

TABLE 3

| | % Acetylsalicylic acid Dissolved at Time Point | | | |
|---|---|---|---|---|
| Sample # | 2 min | 8 min | 15 min | 30 min |
| 1 | 73% | 93% | 96% | 95% |
| 2 | 35% | 92% | 98% | 98% |
| 3 | 67% | 95% | 97% | 97% |
| 4 | 38% | 89% | 96% | 97% |
| 5 | 55% | 92% | 98% | 98% |
| 6 | 35% | 94% | 99% | 100% |

TABLE 4

| | % Pseudoephedrine HCl Dissolved at Time Point | | | |
|---|---|---|---|---|
| Sample # | 2 min | 8 min | 15 min | 30 min |
| 1 | 104% | 109% | 110% | 110% |
| 2 | 102% | 102% | 102% | 102% |
| 3 | 100% | 105% | 105% | 105% |
| 4 | 16% | 66% | 97% | 112% |
| 5 | 15% | 54% | 92% | 104% |
| 6 | 13% | 55% | 87% | 100% |

Figure 4A:
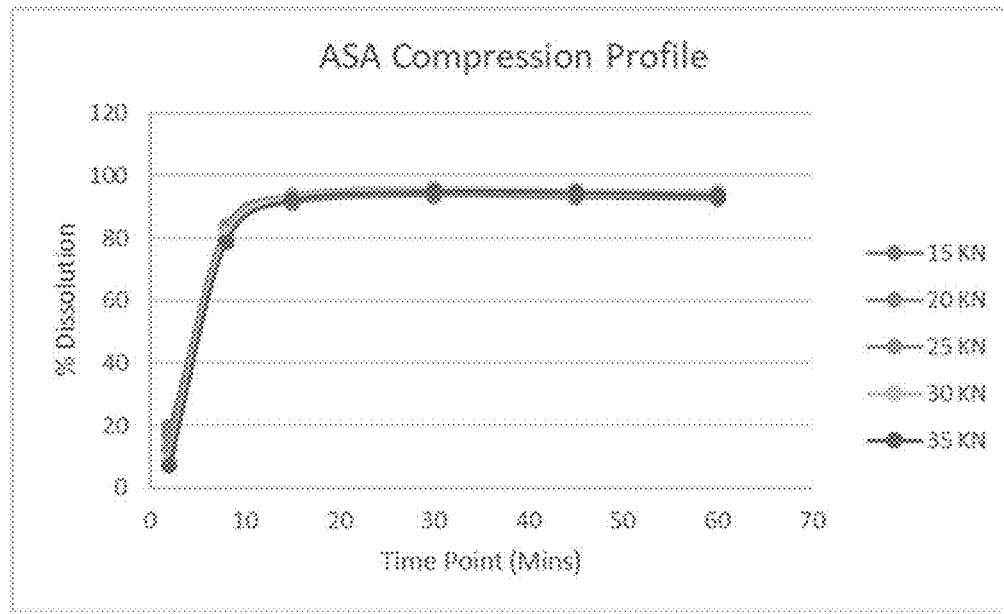
FIGS. 4A and 4B show dissolution profiles of bilayer tablets prepared under different compression forces.
Figure 4B:
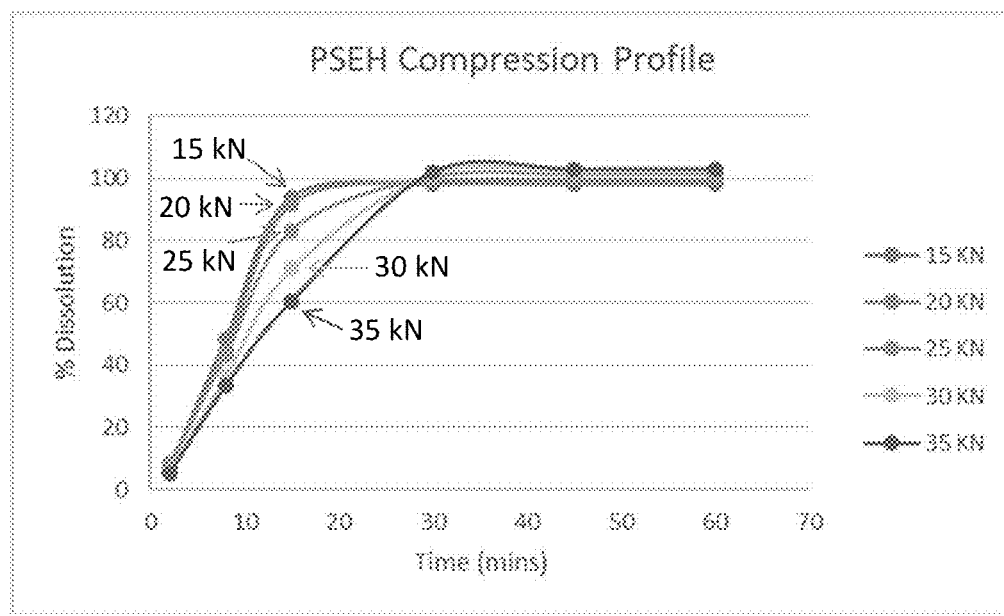

In further studies, the acetylsalicylic acid and pseudoephedrine hydrochloride dissolution profiles of bilayer tablets (Sample #4 formulation) prepared under different tableting compression forces were evaluated. The observed average percentage dissolution of acetylsalicylic acid and pseudoephedrine hydrochloride are shown in Table 8 after 60 minutes. The dissolution profiles for each active ingredient at time points 10 minutes, 20 minutes, 30 minutes, 40 minutes, 50 minutes and 60 minutes are depicted in FIGS. 4A and 4B. Table 5 below shows the percentages of acetylsalicylic acid and pseudoephedrine hydrochloride dissolved at 60 minutes. As shown in FIGS. 4A and 4B and Table 5, the dissolution profile of acetylsalicylic acid was similar across all compression forces but pseudoephedrine hydrochloride showed slightly slower dissolution rates in the first 30 minutes with increasing compression force.

TABLE 5

| Compression Force (kN) | % ASA Dissolved at 60 min | % PSEH Dissolved at 60 min |
|---|---|---|
| 15 | 97.00 | 100.70 |
| 20 | 97.96 | 101.23 |
| 25 | 98.98 | 100.96 |
| 30 | 98.03 | 103.15 |
| 35 | 97.65 | 102.83 |
| Average | 97.93 | 101.77 |
| % RSD | 0.7 | 1.1 |

Example 4: Short-Term and Long-Term Storage Stability and Dissolution Studies

The present examples describes stability and dissolution studies of various bilayer tablet formulations after short-term and long-term storage.

Each of the six formulations in Table 2 were subjected to accelerated stability test conditions, kept at 50° C. and 65% relative humidity for twenty (20) days, with the quantities of acetylsalicylic acid (ASA), pseudoephedrine hydrochloride (PSEH), and their respective major degradation products measured at specific time points (days 0 [initial], 5, 10 and 20). The amounts of acetylsalicylic acid, pseudoephedrine hydrochloride, and their respective major degradation products were determined by HPLC analysis as described in Example 2 above.

Degradation products observed in the accelerated stability tests include free salicylic acid (FSA), acetylsalicylsalicylic acid (ASSA), N-acetyl pseudoephedrine (PSEH-N ester), O-acetyl pseudoephedrine (PSEH-O ester), and N,O-acetyl pseudoephedrine (PSEH diester). Table 6 below shows the average percentages of acetylsalicylic acid, pseudoephedrine hydrochloride, and a selection of degradation products observed at each time point for three individual tablets for each bilayer formulation sample.

As compared to the samples #1-3, in which sodium carbonate was localized in the acetylsalicylic acid layer, a distribution of sodium carbonate across both layers of the bilayer tablet in samples #4-6 resulted in higher quantities of remaining acetylsalicylic acid in the tablet after storage for 20 days.

In a series of further experiments, the same six formulations of Table 2 were subjected to additional long-term stability studies (either at 40° C. and 75% relative humidity or 25° C. and 60% relative humidity) with and without desiccant. Following storage for a fixed period of time, the bilayer tablets tested were evaluated for the amounts of acetylsalicylic acid and pseudoephedrine hydrochloride remaining and for the presence of degradation products in accordance with the protocol described in Example 4 above.

Table 7 shows the variable stability conditions and the corresponding table(s) (Tables 8, 10-14, and 16) of degradation results. Dissolution profiles were recorded for the six formulations after storage at one month and 3 months at 40° C. and 75% relative humidity, without desiccant. The dissolution test results observed after 1 month and 3 months in storage are shown in Table 9 and Table 15, respectively.

TABLE 6

| Sample # | Time | % w/w | | | | | | | |
|---|---|---|---|---|---|---|---|---|---|
| | | PSEH | ASA | FSA | ASSA | Total ASA Degs | PSEH-N and O-ester | PSEH Diester | Total PSEH Degs |
| 1 | Initial | 110.5 | 97.2 | 0.84 | 0.14 | 1.0 | 0.15 | 0.02 | 0.2 |
| | Day 5 | 108.7 | 93.6 | 3.00 | 0.53 | 3.9 | 0.67 | 0.49 | 1.2 |
| | Day 10 | 114.0 | 92.7 | 3.80 | 0.53 | 4.8 | 0.95 | 0.94 | 1.9 |
| | Day 20 | 109.5 | 90.4 | 4.71 | 0.53 | 5.7 | 1.21 | 1.81 | 3.0 |
| 2 | Initial | 100.9 | 98.4 | 0.76 | 0.10 | 0.9 | 0.11 | ND | 0.1 |
| | Day 5 | 105.7 | 92.7 | 2.07 | 0.36 | 2.6 | 0.70 | 0.43 | 1.1 |
| | Day 10 | 104.4 | 94.5 | 2.49 | 0.37 | 3.2 | 0.90 | 0.86 | 1.8 |
| | Day 20 | 108.7 | 90.3 | 3.14 | 0.36 | 3.8 | 1.45 | 1.67 | 3.1 |
| 3 | Initial | 104.0 | 99.8 | 0.76 | 0.08 | 0.9 | 0.17 | ND | 0.2 |
| | Day 5 | 103.7 | 96.6 | 2.86 | 0.49 | 3.7 | 0.73 | 0.54 | 1.3 |
| | Day 10 | 106.3 | 95.9 | 3.55 | 0.48 | 4.4 | 0.91 | 1.17 | 2.1 |
| | Day 20 | 103.2 | 92.3 | 4.56 | 0.47 | 5.5 | 1.10 | 2.02 | 3.1 |
| 4 | Initial | 111.1 | 97.1 | 0.78 | 0.09 | 0.9 | 0.17 | 0.02 | 0.2 |
| | Day 5 | 109.9 | 96.2 | 1.85 | 0.24 | 2.3 | 1.56 | 0.81 | 2.4 |
| | Day 10 | 107.7 | 94.3 | 2.10 | 0.24 | 2.5 | 1.88 | 1.34 | 3.2 |
| | Day 20 | 110.6 | 93.7 | 2.65 | 0.29 | 3.2 | 2.39 | 2.43 | 4.8 |
| 5 | Initial | 108.1 | 100.4 | 0.72 | 0.07 | 0.9 | 0.19 | ND | 0.2 |
| | Day 5 | 102.6 | 98.1 | 2.07 | 0.29 | 2.5 | 1.89 | 0.95 | 2.8 |
| | Day 10 | 100.3 | 98.0 | 2.51 | 0.33 | 3.1 | 2.16 | 1.89 | 4.0 |
| | Day 20 | 102.3 | 95.6 | 3.31 | 0.36 | 4.0 | 2.68 | 3.05 | 5.7 |
| 6 | Initial | 102.6 | 101.2 | 0.56 | 0.10 | 0.7 | 0.05 | ND | 0.1 |
| | Day 5 | 100.7 | 99.4 | 2.12 | 0.36 | 2.7 | 1.54 | 0.75 | 2.3 |
| | Day 10 | 98.0 | 99.5 | 2.75 | 0.36 | 3.4 | 2.11 | 1.68 | 3.8 |
| | Day 20 | 98.0 | 95.9 | 3.69 | 0.39 | 4.4 | 2.77 | 2.95 | 5.7 |

TABLE 7

| Table # | Storage Duration | Storage Conditions | Desiccant (with-yes; without-no) | Dissolution Profile |
|---|---|---|---|---|
| Table 8 | 1 month | 40° C., 75% RH | without | Table 9 |
| Table 10 | 1 month, 3 weeks | 40° C., 75% RH | with and without | n/a |
| Table 11 | 1 month, 3 weeks | 25° C., 60% RH | with and without | n/a |
| Table 12 | 3 months | 40° C., 75% RH | with and without | n/a |
| Table 13 | 3 months | 25° C., 60% RH | with and without | n/a |
| Table 14 | 3 months | 40° C., 75% RH | without | Table 15 |
| Table 16 | 3 months | 25° C., 60% RH | without | n/a |

TABLE 8

| | % w/w | | | | | | | |
|---|---|---|---|---|---|---|---|---|
| Sample # | PSEH | ASA | FSA | ASSA | Total ASA Degs | PSEH-N and O-ester | PSEH Diester | Total PSEH Degs |
| 1 | 114.6 | 94.4 | 2.90 | 0.36 | 3.4 | 0.67 | 0.52 | 1.2 |
| 2 | 100.5 | 96.3 | 1.86 | 0.18 | 2.1 | 0.73 | 0.51 | 1.2 |
| 3 | 105.8 | 96.2 | 2.49 | 0.29 | 2.9 | 0.73 | 0.58 | 1.3 |
| 4 | 110.4 | 95.8 | 1.72 | 0.16 | 1.9 | 1.16 | 0.73 | 1.9 |
| 5 | 103.6 | 99.2 | 2.04 | 0.21 | 2.3 | 1.49 | 1.03 | 2.5 |
| 6 | 95.2 | 100.8 | 2.11 | 0.23 | 2.4 | 1.34 | 0.87 | 2.2 |

TABLE 9

| | % ASA Dissolution at Time Point (average) | | | | % PSEH Dissolution at Time Point (average) | | | |
|---|---|---|---|---|---|---|---|---|
| Sample # | 2 min | 8 min | 15 min | 30 min | 2 min | 8 min | 15 min | 30 min |
| 1 | 65 | 89 | 92 | 92 | 99 | 113 | 114 | 114 |
| 2 | 50 | 91 | 94 | 93 | 99 | 105 | 105 | 105 |
| 3 | 73 | 91 | 94 | 93 | 89 | 106 | 107 | 107 |
| 4 | 41 | 86 | 92 | 92 | 9 | 38 | 85 | 107 |
| 5 | 50 | 92 | 96 | 96 | 10 | 44 | 87 | 107 |
| 6 | 34 | 92 | 97 | 97 | 11 | 38 | 70 | 95 |

As shown in Table 8, the sodium carbonate distribution of 30:70 in sample #4 as compared to 50:50 in samples #5 and 6 resulted in less formation of free salicylic acid and other major acetylsalicylic acid-derived degradation products after storage. The dissolution profiles of the bilayer tablets after storage in Table 9 were comparable to the dissolution profiles observed in Table 3 and Table 4, which recorded for tablets that were not subjected to storage conditions.

TABLE 10

| | | % w/w | | | | | | | | |
|---|---|---|---|---|---|---|---|---|---|---|
| | Desiccant | | | | | Total ASA | PSEH-ester | | PSEH | Total PSEH |
| Sample # | Yes/No | PSEH | ASA | FSA | ASSA | Degs | N | O | Diester | Degs |
| 1 | N | 113.1 | 94.5 | 3.33 | 0.36 | 3.9 | 0.36 | 0.41 | 0.66 | 1.4 |
|   | Y | 111.4 | 97.6 | 1.65 | 0.65 | 2.6 | 0.20 | 0.40 | 0.35 | 1.0 |
| 2 | N | 103.3 | 96.2 | 2.20 | 0.18 | 2.5 | 0.41 | 0.47 | 0.69 | 1.6 |
|   | Y | 105.1 | 97.9 | 1.27 | 0.29 | 1.7 | 0.11 | 0.41 | 0.31 | 0.8 |
| 3 | N | 107.9 | 94.8 | 2.90 | 0.28 | 3.3 | 0.35 | 0.34 | 0.78 | 1.5 |
|   | Y | 103.3 | 98.6 | 1.37 | 0.59 | 2.2 | 0.24 | 0.41 | 0.37 | 1.0 |
| 4 | N | 109.5 | 95.1 | 1.98 | 0.16 | 2.2 | 1.31 | <LOQ | 1.04 | 2.4 |
|   | Y | 111.7 | 96.9 | 1.24 | 0.25 | 1.6 | 0.97 | <LOQ | 0.33 | 1.3 |
| 5 | N | 102.2 | 99.0 | 2.39 | 0.21 | 2.7 | 1.55 | <LOQ | 1.39 | 2.9 |
|   | Y | 104.7 | 100.8 | 1.35 | 0.36 | 1.9 | 1.35 | <LOQ | 0.47 | 1.8 |
| 6 | N | 99.7 | 99.9 | 2.48 | 0.23 | 2.9 | 1.44 | <LOQ | 1.22 | 2.7 |
|   | Y | 101.1 | 102.2 | 1.46 | 0.39 | 2.0 | 1.19 | <LOQ | 0.33 | 1.5 |

*LOQ = Limit of quantification

TABLE 11

| | | | | | | Total ASA | PSEH-ester | | PSEH | Total PSEH |
|---|---|---|---|---|---|---|---|---|---|---|
| | Desiccant | | | | | | | | | |
| Sample # | Yes/No | PSEH | ASA | FSA | ASSA | Degs | N | O | Diester | Degs |
| 1 | N | 113.1 | 96.9 | 1.57 | 0.21 | 1.8 | 0.23 | 0.11 | 0.14 | 0.5 |
|   | Y | 112.9 | 96.7 | 1.07 | 0.19 | 1.3 | 0.10 | 0.12 | 0.08 | 0.3 |
| 2 | N | 100.3 | 98.4 | 1.14 | 0.13 | 1.3 | 0.14 | 0.11 | 0.11 | 0.4 |
|   | Y | 104.6 | 98.2 | 0.86 | 0.12 | 1.0 | 0.05 | 0.12 | 0.05 | 0.2 |
| 3 | N | 107.6 | 98.8 | 1.25 | 0.17 | 1.4 | 0.24 | 0.10 | 0.16 | 0.5 |
|   | Y | 104.8 | 100.7 | 0.83 | 0.15 | 1.0 | 0.14 | 0.13 | 0.08 | 0.4 |
| 4 | N | 112.4 | 97.7 | 1.03 | 0.12 | 1.2 | 0.44 | <LOQ | 0.11 | 0.6 |
|   | Y | 113.2 | 96.0 | 0.85 | 0.11 | 1.0 | 0.36 | <LOQ | 0.09 | 0.5 |
| 5 | N | 103.2 | 100.4 | 1.07 | 0.11 | 1.2 | 0.61 | <LOQ | 0.17 | 0.8 |
|   | Y | 104.0 | 99.6 | 0.83 | 0.10 | 0.9 | 0.50 | <LOQ | 0.12 | 0.6 |
| 6 | N | 100.0 | 101.9 | 1.17 | 0.15 | 1.3 | 0.57 | <LOQ | 0.14 | 0.7 |
|   | Y | 102.7 | 100.8 | 0.91 | 0.14 | 1.1 | 0.44 | <LOQ | 0.09 | 0.5 |

*LOQ = Limit of quantification

TABLE 12

| | | | | | | Total ASA | PSEH-ester | | PSEH | Total PSEH |
|---|---|---|---|---|---|---|---|---|---|---|
| | Desiccant | | | | | | | | | |
| Sample # | Yes/No | PSEH | ASA | FSA | ASSA | Degs | N | O | Diester | Degs |
| 1 | N | 111.6 | 93.1 | 3.83 | 0.34 | 4.4 | 0.32 | 0.53 | 0.62 | 1.5 |
|   | Y | 111.3 | 93.7 | 1.75 | 0.86 | 3.1 | 0.22 | 0.57 | 0.30 | 1.1 |
| 2 | N | 104.5 | 95.0 | 2.53 | 0.18 | 2.8 | 0.42 | 0.62 | 0.65 | 1.7 |
|   | Y | 98.8 | 96.9 | 1.24 | 0.36 | 1.8 | 0.20 | 0.64 | 0.24 | 1.1 |
| 3 | N | 103.3 | 95.4 | 3.29 | 0.29 | 3.8 | 0.33 | 0.51 | 0.69 | 1.5 |
|   | Y | 102.0 | 96.6 | 1.46 | 0.78 | 2.6 | 0.27 | 0.47 | 0.31 | 1.0 |
| 4 | N | 106.8 | 95.5 | 2.43 | 0.17 | 2.7 | 1.57 | 0.04 | 1.03 | 2.6 |
|   | Y | 112.4 | 95.9 | 1.32 | 0.31 | 1.8 | 1.19 | 0.04 | 0.32 | 1.5 |
| 5 | N | 101.8 | 97.6 | 2.89 | 0.22 | 3.3 | 1.72 | 0.06 | 1.23 | 3.0 |
|   | Y | 102.2 | 98.4 | 1.44 | 0.49 | 2.2 | 1.47 | 0.06 | 0.40 | 1.9 |
| 6 | N | 98.6 | 98.5 | 2.97 | 0.24 | 3.4 | 1.67 | 0.06 | 1.06 | 2.8 |
|   | Y | 100.9 | 98.4 | 1.42 | 0.47 | 2.2 | 1.21 | 0.06 | 0.28 | 1.5 |

TABLE 13

| | | | | | | Total ASA | PSEH-ester | | PSEH | Total PSEH |
|---|---|---|---|---|---|---|---|---|---|---|
| | Desiccant | | | | | | | | | |
| Sample # | Yes/No | PSEH | ASA | FSA | ASSA | Degs | N | O | Diester | Degs |
| 1 | N | 113.6 | 96.6 | 1.75 | 0.25 | 2.0 | 0.30 | 0.13 | 0.06 | 0.5 |
|   | Y | 114.5 | 96.5 | 1.02 | 0.23 | 1.3 | 0.15 | 0.14 | 0.00 | 0.3 |
| 2 | N | 104.7 | 95.4 | 1.17 | 0.14 | 1.3 | 0.26 | 0.15 | 0.03 | 0.4 |
|   | Y | 109.8 | 96.2 | 0.78 | 0.14 | 0.9 | 0.13 | 0.14 | 0.02 | 0.3 |
| 3 | N | 103.8 | 98.9 | 1.47 | 0.19 | 1.7 | 0.30 | 0.11 | 0.06 | 0.5 |
|   | Y | 105.6 | 99.4 | 0.81 | 0.20 | 1.0 | 0.16 | 0.14 | 0.01 | 0.3 |
| 4 | N | 111.2 | 96.4 | 1.12 | 0.13 | 1.3 | 0.66 | ND | 0.06 | 0.7 |
|   | Y | 114.7 | 97.5 | 0.83 | 0.13 | 1.0 | 0.53 | 0.01 | 0.01 | 0.5 |
| 5 | N | 98.3 | 100.5 | 1.24 | 0.14 | 1.4 | 0.86 | ND | 0.10 | 1.0 |
|   | Y | 103.6 | 101.2 | 0.79 | 0.13 | 0.9 | 0.52 | 0.01 | 0.01 | 0.5 |
| 6 | N | 102.7 | 101.6 | 1.32 | 0.17 | 1.5 | 0.75 | ND | 0.07 | 0.8 |
|   | Y | 102.7 | 100.8 | 0.84 | 0.17 | 1.0 | 0.17 | ND | 0.01 | 0.2 |

*ND = not detected

Table 10, Table 11, Table 12, and Table 13 show the observed amounts of degradation products after storage with or without desiccant. As shown in the Tables, the inclusion of desiccant during storage appeared to reduce the formation of several major degradation products, including free salicylic acid, total acetylsalicylic acid degradation products, N-acetyl pseudoephedrine, N,O-acetyl pseudoephedrine diester, and total pseudoephedrine degradation products. Desiccant did not appear to affect the formation of acetylsalicylsalicylic acid under storage conditions of 25° C. and 60% RH.

TABLE 14

| | % w/w | | | | | | | | |
|---|---|---|---|---|---|---|---|---|---|
| | | | | | Total ASA | PSEH-ester | | | Total PSEH |
| Sample # | PSEH | ASA | FSA | ASSA | Degs | N | O | PSEH Diester | Degs |
| 1 | 109.3 | 92.0 | 4.46 | 0.33 | 5.2 | 0.87 | 0.08 | 4.69 | 5.6 |
| 2 | 102.5 | 91.1 | 3.22 | 0.18 | 3.7 | 1.03 | 0.14 | 4.84 | 6.0 |
| 3 | 102.4 | 93.7 | 4.04 | 0.27 | 4.70 | 0.81 | 0.08 | 5.03 | 5.9 |
| 4 | 109.5 | 91.6 | 3.03 | 0.20 | 3.52 | 0.05 | 2.13 | 6.33 | 8.5 |
| 5 | 98.9 | 96.2 | 3.51 | 0.24 | 4.13 | 0.06 | 2.06 | 7.43 | 9.5 |
| 6 | 95.3 | 96.6 | 3.57 | 0.25 | 4.2 | 0.06 | 1.89 | 6.86 | 8.8 |

TABLE 15

| Sample # | % ASA Dissolution at Time Point (average) | | | | % PSEH Dissolution at Time Point (average) | | | |
|---|---|---|---|---|---|---|---|---|
| | 2 min | 8 min | 15 min | 30 min | 2 min | 8 min | 15 min | 30 min |
| 1 | 57 | 75 | 80 | 84 | 88 | 107 | 109 | 111 |
| 2 | 45 | 76 | 81 | 84 | 73 | 93 | 97 | 99 |
| 3 | 46 | 74 | 78 | 81 | 77 | 101 | 102 | 102 |
| 4 | 28 | 80 | 87 | 88 | 10 | 27 | 54 | 98 |
| 5 | 24 | 72 | 76 | 77 | 8 | 39 | 82 | 93 |
| 6 | 23 | 80 | 85 | 87 | 7 | 31 | 66 | 89 |

Table 14 shows that the acetylsalicylic acid-derived degradation products formed after 3 months of storage at 40° C. and 75% RH, were present at nearly similar weight percentages as observed under accelerated storage conditions on Day 20 (in Table 6). However, the pseudoephedrine diester and total pseudoephedrine degradation products were present in significantly higher quantities as compared to amounts observed the accelerated storage conditions on Day 20 (in Table 6). As shown in Table 15, the total dissolution of acetylsalicylic acid at 30 minutes was on average reduced as compared to the dissolution at the same time point in Table 3 (not subjected to storage conditions) and in Table 9 (subjected to 1 month at same storage conditions, 40° C., 75% RH, without desiccant). Table 16 shows observed degradation products after 3 months of storage at storage conditions of 25° C. and 60% RH. After storage at conditions of 25° C. and 60% RH, the quantities of free salicylic acid, pseudoephedrine diester, and total pseudoephedrine degradation products were increased relative to the same amounts present in tablets not subjected to storage (in Table 6, initial time point).

TABLE 16

| | % w/w | | | | | | | | |
|---|---|---|---|---|---|---|---|---|---|
| | | | | | Total ASA | PSEH-ester | | | Total PSEH |
| Sample # | PSEH | ASA | FSA | ASSA | Degs | N | O | PSEH Diester | Degs |
| 1 | 97.8 | 102.3 | 1.59 | 0.20 | 1.9 | ND | 0.15 | 0.64 | 0.8 |
| 2 | 106.4 | 99.2 | 1.51 | 0.16 | 1.8 | ND | 0.10 | 0.47 | 0.6 |
| 3 | 109.1 | 98.2 | 1.34 | 0.14 | 1.6 | ND | 0.13 | 0.64 | 0.8 |
| 4 | 103.6 | 96.7 | 1.78 | 0.22 | 2.1 | 0.05 | 0.76 | 0.79 | 1.6 |
| 5 | 104.8 | 96.4 | 1.42 | 0.16 | 1.7 | 0.04 | 0.97 | 0.99 | 2.0 |
| 6 | 115.0 | 93.8 | 2.12 | 0.27 | 2.6 | 0.05 | 0.77 | 0.88 | 1.7 |

*ND = not detected

Example 5: Dissolution Profile Comparison of Various Acetylsalicylic Acid Formulations In this example, various commercial acetylsalicylic acid formulations were assessed for their acetylsalicylic acid dissolution profiles as compared to the bilayer tablets provided herein to evaluate the effects of various physical formulation parameters (granulated vs non-granulated; single layer vs bilayer) on dissolution rate.

Five separate samples were subjected to the dissolution test protocol described in Example 3 above. The samples included: (A) the bilayer tablet formulation described in Table 1 (Example 1) including both acetylsalicylic acid and pseudoephedrine HCl layers; (B) a single layer tablet formulated identically to the acetylsalicylic acid sub-layer described in Table 1 (Example 1); (C) a single layer tablet comprising only granulated acetylsalicylic acid (74.85% w/w acetylsalicylic acid, 24.7% w/w sodium carbonate, 0.45% w/w colloidal silicon dioxide, trace coating); (D) granules comprising acetylsalicylic acid and pseudoephedrine HCl (500 mg acetylsalicylic acid; 30 mg pseudoephedrine HCl; citric acid anhydrous, sucrose, hypromellose, saccharin, flavor, maltodextrin); and (E) acetylsalicylic acid, corn starch, hypromellose, powdered cellulose, triacetin.

Figure 5:
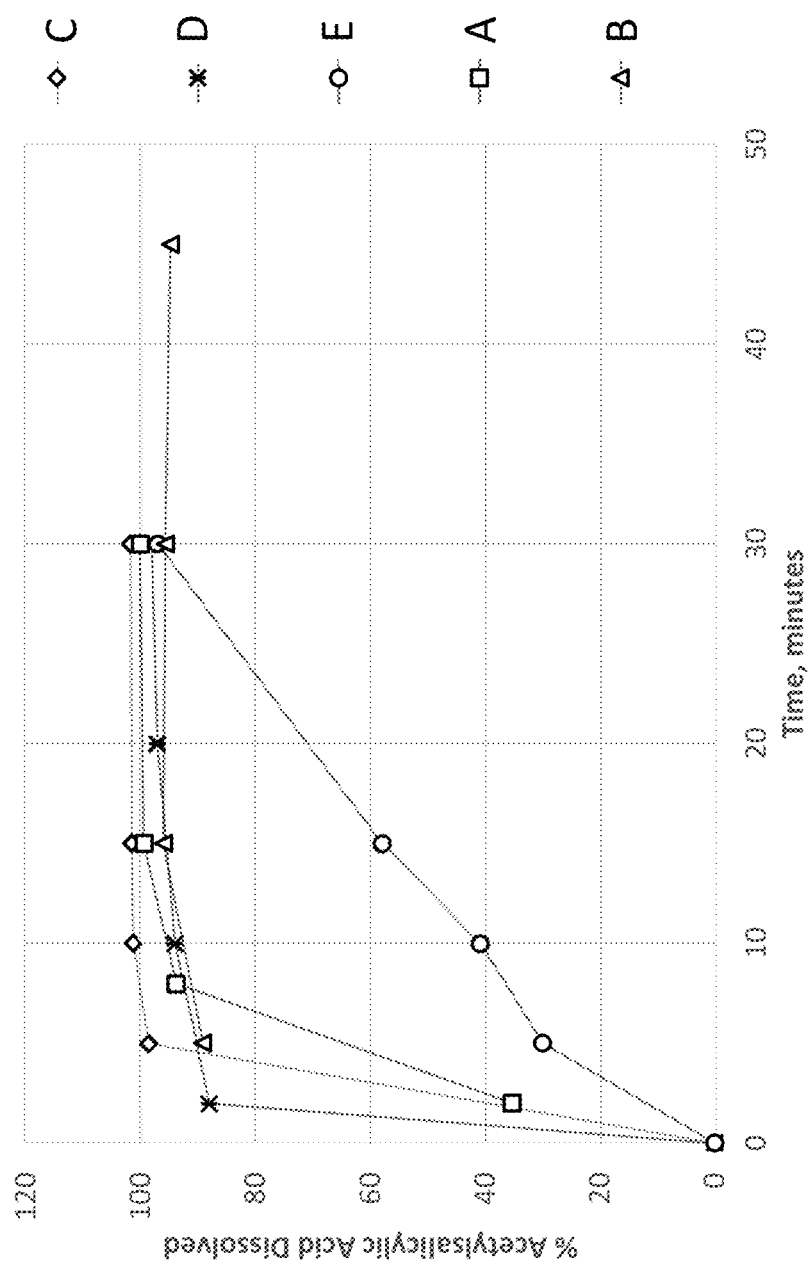
FIG. 5 depicts dissolution profiles of acetylsalicylic acid prepared in various formulations.

FIG. 5 shows the dissolution profiles of acetylsalicylic acid prepared in various formulations.

Example 6: Phenylephrine Substitution for Pseudoephedrine

In additional experiments, phenylephrine hydrochloride was employed as a substitute for pseudoedphedrine hydrochloride as a decongestant in Layer II. Four sample bilayer tablet formulations were prepared using phenylephrine hydrochloride in accordance with the preparation protocol of Example 1, with the ratios of granulated acetylsalicylic acid (intragranular, "INTRA") to non-granulated acetylsalicylic acid (extragranular, "EXTRA") within the acetylsalicylic acid layer and distributions of sodium carbonate throughout the acetylsalicylic acid and phenylephrine layers as described in Table 17 below. All four formulations contained a fixed quantity of 500 mg acetylsalicylic acid (ASA), 30 mg phenylephrine hydrochloride (PEH), and 165 mg sodium carbonate ($Na_2CO_3$). In sample #9, all sodium carbonate in the acetylsalicylic acid layer (Layer I) was contained within the granulated acetylsalicylic acid.

TABLE 17

| | | | | $Na_2CO_3$ | | |
|---|---|---|---|---|---|---|
| | Acetylsalicylic acid | | | ASA Layer | PEH Layer | |
| Sample # | INTRA (mg) | EXTRA (mg) | Intra:Extra Ratio | (I) (mg) | (II) (mg) | Layer I:Layer II Ratio |
| 7 | 0 | 500 | 0:100 | 82.5 | 82.50 | 50:50 |
| 8 | 0 | 500 | 0:100 | 0 | 165 | 0:100 |
| 9 | 150 | 350 | 30:70 | 49.5 | 115.5 | 30:70 |
| 10 | 0 | 500 | 0:100 | 49.5 | 115.5 | 30:70 |

The same dissolution test parameters as described in Example 2 were utilized to evaluate the bilayer tablets comprising phenylephrine. Aliquots were taken at time points of 5 minutes, 15 minutes, 30 minutes and 45 minutes. Three bilayer tablet trials were carried out for each sample formulation (n=3). Table 18 and Table 19 respectively show the observed average dissolution of acetylsalicylic acid and phenylephrine hydrochloride at each time point. The quantity of acetylsalicylic acid dissolved at each time point was determined by UV absorption spectrometry at detection wavelength 257 nm. The quantity of phenylephrine hydrochloride dissolved at each time point was determined by UV absorption spectrometry at detection wavelength 214 nm.

TABLE 18

| % Acetylsalicylic acid Dissolved at Time Point | | | | |
|---|---|---|---|---|
| Sample # | 5 min | 15 min | 30 min | 45 min |
| 7 | 89% | 96% | 96% | 95% |
| 8 | 53% | 85% | 97% | 99% |
| 9 | 84% | 94% | 94% | 93% |
| 10 | 84% | 92% | 91% | 91% |

TABLE 19

| % Phenylephrine HCl Dissolved at Time Point | | | | |
|---|---|---|---|---|
| Sample # | 5 min | 15 min | 30 min | 45 min |
| 7 | 71% | 107% | 108% | 108% |
| 8 | 41% | 85% | 98% | 98% |
| 9 | 55% | 102% | 108% | 107% |
| 10 | 54% | 102% | 108% | 108% |

Further to the dissolution assays, the four phenylephrine-containing bilayer tablets (Samples #7-10) and four additional samples (Samples #11-14), the compositions of which are detailed in Table 20, were subjected to accelerated stability test conditions at (storage at 50° C. at a 65% relative humidity for 20 days) to gauge susceptibility to degradation. The formation of degradation products was determined using the protocol described in Examples 2 and 4 above.

TABLE 20

| | | | | $Na_2CO_3$ | | |
|---|---|---|---|---|---|---|
| | Acetylsalicylic acid | | | ASA Layer | PEH Layer | |
| Sample # | INTRA (mg) | EXTRA (mg) | Intra:Extra Ratio | (I) (mg) | (II) (mg) | Layer I:Layer II Ratio |
| 11 | 150 | 350 | 30:70 | 49.5 | 115.5 | 30:70 |
| 12 | 150 | 350 | 30:70 | 0 | 165 | 0:100 |
| 13 | 150 | 350 | 30:70 | 49.5 | 115.5 | 30:70 |
| 14 | 150 | 350 | 30:70 | 0 | 165 | 0:100 |

Table 21 presents the observed quantity of free salicylic acid for each tablet formulation after storage under accelerated stability test conditions. As shown in Table 18, Table 19, and Table 21, sample #8, prepared with no intragranular acetylsalicylic acid and all sodium carbonate localized in the phenylephrine layer, resulted in the lowest formation of free salicylic acid but also gave the slowest dissolution profile relative to samples #7 and 9-10. Similarly, in samples #11-14, the samples with sodium carbonate localized to the phenylephrine layer resulted in less free salicylic acid formation.

TABLE 21

| Sample # | % w/w free salicylic acid |
|---|---|
| 7 | 1.26 |
| 8 | 0.35 |
| 9 | 1.10 |
| 10 | 1.00 |
| 11 | 2.62 |
| 12 | 1.67 |
| 13 | 1.86 |
| 14 | 1.02 |

What is claimed is:

1. A bilayer tablet, comprising:
an acetylsalicylic acid layer, comprising:
granules, wherein the granules comprise intragranular acetylsalicylic acid, intragranular sodium carbonate, and one or more intragranular excipients;
extragranular acetylsalicylic acid; and
one or more extragranular excipients; and
a pseudoephedrine layer, comprising:
pseudoephedrine or a pharmaceutically acceptable salt thereof;
sodium carbonate; and
one or more excipients;
wherein 10-50% w/w of the total acetylsalicylic acid present in the tablet is intragranular acetylsalicylic acid, and
wherein the tablet has a weight ratio of the acetylsalicylic acid to sodium carbonate of between 1:1 and 5:1.

2. The tablet of claim 1, wherein the tablet has a weight ratio of acetylsalicylic acid to sodium carbonate between 2:1 and 4:1.

3. The tablet of claim 1, wherein 10-50% w/w of the total sodium carbonate present in the tablet is intragranular sodium carbonate.

4. The tablet of claim 1, wherein 20-40% w/w of the total acetylsalicylic acid present is intragranular acetylsalicylic acid.

5. The tablet of claim 1, wherein 20-40% w/w of the total sodium carbonate present in the tablet is present in the acetylsalicylic acid layer.

6. The tablet of claim 1, comprising between 250 mg and 1000 mg acetylsalicylic acid.

7. The tablet of claim 1, comprising between 15 mg and 60 mg pseudoephedrine or a pharmaceutically acceptable salt thereof.

8. The tablet of claim 1, wherein the one or more intragranular excipients in the granules comprises colloidal silicon dioxide.

9. The tablet of claim 1, wherein the one or more extragranular excipients in the acetylsalicylic acid layer comprises colloidal silicon dioxide, cornstarch, and cellulose.

10. The tablet of claim 1, wherein the one or more excipients in the pseudoephedrine layer comprises mannitol, microcrystalline cellulose, cornstarch, and colloidal silicon dioxide.

11. The tablet of claim 1, further comprising a coating.

12. The tablet of claim 1, wherein the tablet comprises less than or equal to 4% w/w salicylic acid of the initial acetylsalicylic acid content after storage at 40° C. and 75% relative humidity for at least 1 month.

13. The tablet of claim 1, wherein the tablet has a dissolution profile wherein at least 85% acetylsalicylic acid and at least 85% pseudoephedrine are dissolved at 10 minutes as determined by USP Dissolution Test (Apparatus 1) in 50 mM sodium acetate buffer at pH 4.5 at 37±0.5° C.

14. A method for preparing a bilayer tablet according to claim 1, comprising:
    compacting and milling acetylsalicylic acid, sodium carbonate, and colloidal silicon dioxide to provide granules;
    combining the granules with acetylsalicylic acid, cornstarch, powdered cellulose, and colloidal silicon dioxide to provide an acetylsalicylic acid blend;
    combining pseudoephedrine or a pharmaceutically acceptable salt thereof, cornstarch, mannitol, sodium carbonate, microcrystalline cellulose and colloidal silicon dioxide to provide a pseudoephedrine blend; and
    compressing the acetylsalicylic acid blend and pseudoephedrine blend to form the bilayer tablet.

15. The method of claim 14, comprising compacting the acetylsalicylic acid, sodium carbonate, and colloidal silicon dioxide by roller compaction.

16. The method of claim 14, wherein the granules have a particle size distribution wherein between 5% w/w and 30% w/w of the granules out of the total granule weight have a particle size of less than 150 µm, and wherein between 50% w/w and 80% w/w of the granules out of the total granule weight have a particle size of greater than 400 µm.

17. The method of claim 14, further comprising drying the acetylsalicylic acid blend prior to compressing.

18. The method of claim 14, wherein compressing the acetylsalicylic acid blend and pseudoephedrine blend to form the bilayer tablet comprises:
    compressing the acetylsalicylic acid blend at a first compression force to provide an acetylsalicylic acid layer; and
    compressing the pseudoephedrine blend on top of the acetylsalicylic acid layer at a second compression force to form the bilayer tablet.

19. The method of claim 14, wherein compressing the acetylsalicylic acid blend and pseudoephedrine blend to form the bilayer tablet comprises:
    compressing the pseudoephedrine blend at a first compression force to provide a pseudoephedrine layer; and
    compressing the acetylsalicylic acid blend on top of the pseudoephedrine layer at a second compression force to form the bilayer tablet.

20. A method for treating nasal congestion and pain or fever in a human in need thereof, comprising administering a bilayer tablet according to claim 1 to the human.

* * * * *